United States Patent
Hook

(10) Patent No.: US 6,313,268 B1
(45) Date of Patent: Nov. 6, 2001

(54) SECRETASES RELATED TO ALZHEIMER'S DEMENTIA

(76) Inventor: Vivian Y. H. Hook, 8276 Caminito Maritimo, La Jolla, CA (US) 92037

( * ) Notice: Subject to any disclaimer, the term of this patent is extended or adjusted under 35 U.S.C. 154(b) by 0 days.

(21) Appl. No.: 09/294,987

(22) Filed: Apr. 20, 1999

Related U.S. Application Data

(63) Continuation-in-part of application No. 09/173,887, filed on Oct. 16, 1998, now Pat. No. 6,245,884.

(51) Int. Cl.$^7$ ............................. C07K 14/00; C12N 9/00; A61K 38/43

(52) U.S. Cl. .......................... 530/350; 530/412; 530/422; 530/427; 435/183; 435/212; 435/226; 424/94.1; 424/94.2; 424/94.6; 424/94.63; 424/94.66; 424/563; 424/570

(58) Field of Search ................................. 424/94.1, 94.2, 424/94.6, 94.63, 94.66, 563, 570; 435/183, 212, 226; 530/350, 412, 422, 427

(56) References Cited

U.S. PATENT DOCUMENTS

| | | |
|---|---|---|
| 5,200,339 | 4/1993 | Abraham . |
| 5,262,332 | 11/1993 | Selkoe ................................. 436/518 |
| 5,604,102 | 2/1997 | McConlogue et al. . |
| 5,703,129 | 12/1997 | Felsenstein et al. . |
| 5,733,768 | 3/1998 | Dixon et al. . |
| 5,744,346 | 4/1998 | Chrysler et al. ..................... 435/226 |
| 5,766,846 | 6/1998 | Schlossmacher et al. ............... 435/6 |
| 5,837,672 | 11/1998 | Schenk et al. ............................ 514/2 |
| 5,942,400 | 8/1999 | Anderson et al. .................... 435/7.1 |

FOREIGN PATENT DOCUMENTS

| | | |
|---|---|---|
| 0 580 161 | 1/1994 | (EP) . |
| 92/00768 | 1/1992 | (WO) . |
| 96/40885 | 12/1996 | (WO) . |
| 98/03642 | 1/1998 | (WO) . |
| 98/13488 | 4/1998 | (WO) . |
| 98/15828 | 4/1998 | (WO) . |
| 98/21589 | 5/1998 | (WO) . |
| 98/26059 | 6/1998 | (WO) . |

OTHER PUBLICATIONS

Moore et al., Exp. Opin. Ther. Patents (1999) 9(2):135–143.*
Sinha et al., Nature (1999) 402:537–540.*
Vassar et al., Science (1999) 286:735–741.*
Chen, M. and Fernandez, H. L. "The Alzheimer's plaques, tangles, and memory deficits may have a common originPart IV: Can Calpain act as α–Secretase?" Frontiers in Bioscience 3, a66–75 (Dec. 15, 1998).
Parvathy et al., "Alzheimer's amyloid precursor protein alpha–secretase is inhibited by hydroxamic acid–based zinz metalloprotease inhibitors: similarities to the angiotensin converting enzyme secretase," Biochemistry 37(6):1680–1685 (1998).
Potts et al., "Proteolytic cleavage of the integrin beta–4 subunit," Exp. Cell Res. 212:2–9 (1994).
Tawaga et al., "Alzheimer's disease amyloid beta–clipping enzyme (APP secretase): identification, purification, and characterization of the enzyme," Biochem. and Biophys. Res. Comm. 177(1):377–387 (1991).
Matsumoto et al., "The 68 kDa human beta–secretase in brains of Alzheimer's disease patients contains heparan sulfate glycoconjugate," Neurobiol. of Aging, 17(4 supp.):S107 Abstract (1996).
Matsumoto et al., "Human brain beta–secretase contains heparan sulfate glycoconjugates," Neurosci. Lett., 211:105–108 (1996).
Berg et al., "Composition of white matter bovine brain coated vesicles: evidence that several components influence β–amyloid peptide to form oligomers and aggregates in vitro," Brain Res. 752:72–80 (1997).
Campbell et al., "Identification of a protein kinase as an intrinsic component of rat liver coated vesicles," Biochem. 23:4420–4426 (1984).
Knops et al., "Evidence for a nonsecretory, acidic degradation pathway for amyloid precursor protein in 293 cells," J. Bio. Chem. 267(23):16022–16024 (1992).
Marks et al., "Hydrolysis of amyloid precursor protein–derived peptides by cysteine proteinases and extracts of rat brain clathrin–coated vesicles," Peptides 15(1):175–182 (1994).
Marks et al., "Brain cathepsin B but not metalloendopeptidases degrade rAPP$^{751}$ with production of amyloidogenic fragments," Int. J. of Peptide & Protein Res. 46:306–313 (1995).
Sambamurti et al., "Evidence for intracellular cleavage of the alzheimer's amyloid precursor in PC12 cells," J. Neuroscience Res. 33:319–329 (1992)1.
Xia et al., "Presenilin 1 regulates the processing of β–amyloid precursor protein c–terminal fragments and the generation of amyloid β–protein in endoplasmic reticulum and golgi," Biochem. 37:16465–16471 (1998).
Abraham, C. et al., "Immunochemical Identification of the Serine Protease Inhibitor α$_1$–Antichymotrypsin in the Brain Amyloid Deposits of Alzheimer's Disease," Cell, 52:487–501 (1988).

(List continued on next page.)

Primary Examiner—Christopher S. F. Low
Assistant Examiner—Stephen Tu
(74) Attorney, Agent, or Firm—Campbell & Flores LLP

(57) ABSTRACT

This invention is directed to a novel β-secretase that produces the Aβ peptide found in Alzheimer's Disease. One β-secretase is a protein having a molecular weight of about 61, 81 or 88 kDa that cleaves an amyloid precursor protein (APP) substrate. Another is a protease complex having a molecular between about 180 and 200 kDa, which, in one embodiment, contains the 61, 81, and 88 kDa proteins and, in another embodiment, contains proteins having a molecular weight of about 66, 60, 33 and 29 kDa. Another β-secretase has a molecular weight between about 50 and 90 kDA. The invention is also directed to methods of selecting agents that inhibit Aβ peptide production and treating Alzheimer's disease in patients.

11 Claims, 8 Drawing Sheets

OTHER PUBLICATIONS

Abraham, C. et al., "Facile and Sensitive Assay for Monitoring Proteolytic Activities with Defined Specificities: Studies on Amyloid β–Protein Processing in Alzheimer's Disease," *Peptide Res.*, 3(5):211–215 (1990).

Azaryan, A. et al., "Characteristics of the Chromaffin Granule Aspartic Proteinase Involved in Proenkephalin Processing," *J. of Neurochem.*, 65(4):1771–1779 (1995).

Azaryan, A. et al., "Chromaffin Granule Aspartic Proteinase Processes Recombinant Proopiomelanocortin (POMC)," *Biochem. Biophys. Res. Commun.*, 215(3):937–944 (1995).

Azaryan, A. et al., "Distinct Properties of Prohormone Thiol Protease (PTP) Compared to Cathepsins B, L, and H: Evidence for PTP as a Novel Cysteine Protease," *Arch. Biochem. Biophys.*, 314(1):171–177 (1994).

Azaryan, A. et al., "Kex2–like Proteolytic Activity in Adrenal Medullary Chromaffin Granules," *Biochem. Biophys. Res. Commun.*, 185(1):398–403 (1992).

Azaryan, A. et al., "Purification and Characteristics of the Candidate Prohormone Processing Proteases PC2 and PC1/3 from Bovine Adrenal Medulla Chromaffin Granules," *J. Biol. Chem.*, 270:8201–8208 (1995).

Azaryan, A. et al., "Unique Cleavage Specificity of 'Prohormone thiol Protease' Related to Proenkephalin Processing," *FEBS Lett.*, 341:197–202 (1994).

Backstrom, J. et al., "Matrix Metalloproteinase–9 (MMP–9) Is Synthesized in Neurons of the Human Hippocampus and Is Capable of Degrading the Amyloid–β Peptide (1–40)," *J. Of Neuroscience*, 16(24):7910–7919 (1996).

Bodovitz, S. et al., "Cholesterol Modulates α–Secretase Cleavage of Amyloid Precursor Protein," *J. Of Biological Chem.*, 271(8):4436–4440 (1996).

Brown, A. et al., "Evaluation of Cathepsins D and G and EC 3.4.24.15 as Candidate β–Secretase Proteases Using Peptide and Amyloid Precursor Protein Substrates," *J. Of Neurochem.*, 66(6):2436–2445 (1996).

Cataldo, A. et al., "Increased Neuronal Endocytosis and Protease Delivery to Early Endosomes in Sporadic Alzheimer's Disease: Neuropathologic Evidence for a Mechanism of Increased β–Amyloidogenesis," *J. Of Neurosci.*, 17(16):6142–6151 (1997).

Chang, T. et al., "A Novel Brain Cysteine Protease Forms and SDS Stable Complex with the β–Amyloid Precurosr Protein$^{\alpha}$," *Ann NY Acad. Sci.*, 777:183–188 (1996).

Chesselet, M. et al., "Carboxypeptidase H–like Immunoreactivity in the Striatum of Cats and Monkeys," *Regulatory Peptides*, 20:151–159 (1988).

Chevallier, N. et al, "Cathepsin D displays in vitro β–secretase–like specificity," *Brain Research*, 750:11–19 (1997).

Citron, M. et al., "Evidence that the 42–and 40–amino acid forms of amyloid β protein are generated from the β–amyloid precursor protein by different protease activities," *Proc. Natl. Acad. Sci. USA*, 93:13170–13175 (1996).

Citron, M. et al., "Generation of Amyloid β protein from Its Precursor Is Sequence Specific," *Neuron.*, 14:661–670 (1995).

Citron, M. et al., "Inhibition of Amyloid β–Protein Production in Neural Cells by the Serine Protease Inhibitor AEBSF," *Neuron*, 17:171–179 (1996).

Cook, D. et al., "Alzheimer's Aβ(1–42) is generated in the endoplasmic reticulum/intermediate comparment of NT2N cells," *Nature Medicine*, 3(9):102–104 (1997).

Desdouits, F. et al., "Amyloid β Peptide Formation in Cell–Free Preparations," *J. Of Biological Chemistry*, 271(40):24670–24674 (1996).

Dugan, J. et al., "The Ras–related GTP–binding Protein, Rab1B, Regulates Early Steps in Exocytic Transport and Processing of β–Amyloid Precursor Protein," *J. Of Biological Chem.*, 270(18):10982–10989 (1995).

Efthimiopoulos, S. et al., "Cholinergic Agonists Stimulate Secretion of Soluble Full–length Amyloid Precurosr Protein in Neuroendocrine Cells," *Proc. Natl. Acad. Sci. USA*, 93:8046–8050 (1996).

Efthimiopoulos, S. et al., "Intracellular Cyclic AMP Inhibits Constitutive and Phorbol Ester–Stimulated Secretory Cleavage of Amyloid precursor Protein," *J. Of Neurochem.*, 67(2):872–875 (1996).

Efthimiopoulos, S. et al., "Localization of Presenilin 1 Peptides in Neuronal Large Dense Core and Somatodendritic Clathin Coated Vesicles," *J. Neurochem.*, 71(6):2365–2372 (1998).

Evin, G. et al., "Candidate γ–Secretases in the Generation of the Carboxyl Terminus of the Alzheimer's Disease βA4 Amyloid: Possible Involvement of Cathepsin D," *Biochemistry*, 34:14185–14192 (1995).

Flagmeyer, I. et al., "General Pharmacology of the Putative Cognition Enhancer Linopirdine," *Arzneim.–Forsch./Drug Res.*, 45(1):456–459 (1995).

Games, D. et al., "Alzheimer–type neuropathology in transgenic mice overexpressing V717F β–amyloid precursor protein," *Nature*, 373:523–527 (1995).

Ghanta, J. et al., "A Strategy for Designing Inhibitors of β–Amyloid Toxicity," *J. Of Biol. Chem.*, 271(47):29525–29528 (1996).

Haass, C. et al., "The Swedish Mutation Causes Early–onset Alzheimer's Disease by B–secretase Cleavage Within the Secretory Pathway," *Nature Medicine*, 1(12):1291–1296 (1995).

Hartmann, T. et al., "Distinct Sites of Intracellular Production for Alzheimer's Disease Aβ40/42 Amyloid Peptides," *Nature Medicine*, 3(9):1016–1020 (1997).

Heisler, S. et al., "Corticotropin Releasing Factor Stimulation of Protein Carboxlmethylation in Mouse Pituitary Tumor Cells," *Biochem. Pharm.*, 32:1295–1299, (1983).

Heisler, S. et al., "Somatostatin Inhibits Multireceptor Stimulation of cyclic AMP Formation and Corticotropin Secretion in Mouse Pituitary Tumor Cells," *Proc. Natl. Acad. Sci. USA*, 79:6502–6506, (1982).

Higaki, J. et al., "Processing of β–Amyloid Precursor Protein by Cathepsin D," *J. Of Biol. Chem.*, 271(50):31885–31893 (1996).

Hines, V. et al., "The Expression And Processing Of Human β–Amyloid Peptide Precursors In *Saccharomyces Cerevisiae*: Evience For A Novel Endopeptidase In The Yeast Secretory System," *Cell. And Mole. Biol. Res.*, 40(4):273–284 (1994).

Ho, L. et al., "The Alternatively Spliced Kunitz Protease Inhibitor Domain Alters Amyloid β Protein Precursor Processing and Amyloid β Protein production in Cultured Cells," *J. Of Biol. Chem.*, 271(48):30929–30934 (1996).

Hook, V. et al., "Partial Purification of Nuclear Protein Kinase from Small Dense Nuclei of Mouse Brain and the Effect of Chronic Morphine Treatment," *J. Neurochem.*, 34:1274–1279, (1980).

Hook, V. et al., "Possible Nuclear Protein Kinase Regulation of Homologous Ribonucleic Acid Polymerases from Small Dense Nuclei of Mouse Brain During Morphine Tolerance–Dependence: Involvement of Cyclic 3', 5'–Adenosine Monophosphate," *Biochem. Pharm.*, 30(16):2313–2318, (1981).

Hook, V. et al., "Evidence for Biochemical Adaptation in Morphine Tolerance Dependence," In: Way El, ed. *Endogenous and Exogenous Opiate Agonists and Antagonist*, New York: Pergamon Press., pp. 493–496.

Hook, V. et al., "A Carboxypeptidase Processing Enzyme for Enkephalin Precursors," *Nature*, 295:341–342, (1982).

Hook, V. et al., "Corticotropin Releasing Factor Stimulates Adrenocorticotropin and B–endorphin Release from Att–20 Mouse Pituitary Tumor Cells," *Biochem. Biophys. Res. Commun.*, 106(4):1364–1371, (1982).

Hook, V. et al., "Corticotropin–releasing Factor Stimulates Phospholipid Methylation and Corticotropin Secretion in Mouse Pituitary Tumor Cells," *Proc. Natl. Acad. Sci. USA.*, 79:6220–6224, (1982).

Hook, V. et al., "Carboxypeptidase B–like Converting Enzyme Activity in Secretory Granules of Rat Pituitary," *Proc. Natl. Acad. Sci. USA*, 81:2776–2780, (1984).

Hook, V. et al., "Carboxypeptidase B–like Activity for the Processing of Enkephalin Precursors in the Membrane Component of Bovine Adrenomedullary Chromaffin Granules," *Neuropeptides*, 4:117–126, (1984).

Hook, V. et al., "Two Peptidases That Convert $^{125}$i–lys–arg–[Met]enkepahlin and $^{125}$i–[Met]enkephalin-arg$^{6,}$ Respectively, to $^{125}$i[met]enkephalin in Bovine Adrenal Medullary Chromaffin Granules," *FEBS LETT*, 72(2):212–218, (1984).

Hook, V. et al., "Immunochemical Characterization of Carboxypeptidase B–like Peptide Hormone–Processing Enzyme," *Proc. Natl. Acad. Sci. USA*, 82:4745–4749, (1985).

Hook, V. et al., "Selective Regulation of Carboxypeptidase Peptide Hormone Processing enzyme during Enkephalin Biosynthesis in Cultured Bovine Adrenomedullary Chromaffin Cells," *J. Biol. Chem.*, 260(10):5991–5997, (1985).

Hook, V. et al., "[Met]enkephalin and Carboxypeptidase Processing Enzyme Are Co–released from Chromaffin Cells by Cholinergic Stimulation," *Biochem. Biophys. Res. Commun.*, 128:563–570, (1985).

Hook, V. et al., "Differential Distribution of Carboxypeptidase Processing Enzyme Activity and Immunoreactivity in Memebrane and Soluble Components of Chromaffin Granules," *J. Neurochem.*, 45(3):987–989, (1985).

Hook, V. et al., "Modulation of Carboxypeptidase Processing Enzyme Activity," In: Moody TW, ed. 5th International Spring Symposium, *Neural and Endocrine Peptides and Receptors*, Pergamon Press, pp. 599–606, (1986).

Hook, V. et al, "Biosynthesis and Maturation of Carboxypeptidase H," *Ann. N.Y. Acad. Sci.*, 493:394–396, (1986).

Hook, V. et al., "Distribution of Enkephlin–Containing Peptides Within Bovine Chromaffin Granules," *Neuropeptides*, 9:263–267, (1987).

Hook, V. et al., "Product Inhibition of Carboxypeptidase H," *J. Biol. Chem.*, 262(26):12583–12588, (1987).

Hook, V. et al., "Regulation of Carboxypeptidase H By Inhibitory and Stimulatory Mechanisms During Neuropeptide Precursor Processing," *Cell. Mol. Neurobiol.*, 8(1):49–55, (1988).

Hook, V. et al., "Differential Regulation of Carboxypeptidase H, a Peptide Precursor Processing Enzyme, and Catecholamines in Adrenal Medulla," In: Sandler M, ed., *Process in Catecholamine Research, Part A: Basic Aspects and Peripheral Mechanisms*, Alan R. Liss, Inc., pp. 263–270, (1988).

Hook, V. et al., "Identification of Zymogen and Mature Forms of Human Carboxypeptidase H: A Processing Enzyme for the Synthesis of Peptide Hormones," *FEBS LETT*, 238(2):338–342, (1988).

Hook, V. et al., "Cleavage of Recominant Enkephalin Precursor By Endoproteolytic Activity in Bovine Chromaffin Granules," *Biochem. Biophys. Res. Commun.*, 167(2):722–730, (1990).

Hook, V. et al., "Arginine and Lysine Product Inhibition of Bovine Adrenomedullary Carboxypeptidase H, A Prohormone Processing Enzyme," *Life Sci.*, 47(2):1135–1139, (1990).

Hook, V. et al., "Carboxypeptidase H in the Hypothalamo––Neurohypophysial System: Evidence for Processing and Activation of a Prohormone–Processing Enzyme During Axonal Transport," *J. Neurosci.*, 10(10):3219–3226, (1990).

Hook, V. et al., "Biosynthesis of Endogenous Opiate Peptides by Proteolytic Precursor Processing Mechanisms," In: Watson R, ed., *Biochemistry and Physiology of Sbstance Abuse*, 3rd ed. Boca Raton: CRC Press, Inc., pp. 367–377, (1991).

Hook, V. et al., "Protease for Neuropeptide Precursor Processing in Bovine Adrenal Medullary Chromaffin Granules," In: Moody TW, ed., *Growth Factors, Peptides and Receptors*, New York: Plenum Press, pp. 61–70, (1993).

Hook, V.Y.H., "Role of a Protease Inhibitor, Antichymotrypsin in Prohormone Processing," *ICOP Newsletter*, (1993).

Hook, V. et al., "Purification and Characterization of $\alpha_1$–Antichymotrypsin–like Protease Inhibitor that Regulates Prohormone Thiol Protease Involved in Enkephalin Precursor Processing," *J. Biol. Chem.*, 268(27):20570–20577, (1993).

Hook, V. et al., "Proteases and the Emerging Role of Protease Inhibitors in Prohormone Processing," *FASEB J.*, 8:1269–1278, (1994).

Hook, V. et al., "The Processing Proteases Prohormone Thiol Protease, PC1/3 and PC2, and 70–kDa Aspartic Proteinase Show Preferences among Proenkephalin, Proneuropeptide Y, and Proopiomelanocortin Substrates," *Arch. Biochem. Biophysics.*, 328(1):107–114, (1996).

Hook, V. et al., "Proenkephalin–processing Enzymes in Chromaffin Granules: A Model for Neuropeptide Biosynthesis," *Ann. N.Y. Acad. Sci.*, 780:121–133, (1996).

Hook, V. et al., "Production of Radiolabeled Neuropeptide Precursors by in vitro Transcription and Translation," *Peptide Research*, 9(4):183–187, (1996).

Hook, V. et al., "High–level Expression of the Prohormones Proendephalin, Pro–neuropeptide Y, Proopiomelanocortin, and β–Protachykinin for In Vitro Prohormone Processing," *Protein Expression Purif.*, 10:80–88, (1997).

Hook, V.Y.H., "Prohormone Processing and $\alpha_1$–antichymotrypsin as a Potential Endognous Inhibitor," In: Macready N, ed., *Protease Inhibitors, Novel Therapeutic Application and Development*, Southborough, MA: IBC Library Series pp. 6.2.1–6.2.22., (1997).

Hook, V.Y.H., "Prohormone Thiol Protease (PTP)," In: Barrett AJ, ed., *Handbook of Proteolytic Enzymes,* Academic Press pp. 779–782, (1998).

Hook, V. et al., "'Prohormone Thiol Protease' (PTP), a novel Cysteine Protease for Proenkephalin and Prohormone Processing," In: Hook, V.Y.H., ed., *Proteolytic and Cellular Mechanisms in Prohormone and Proprotein Processing,* Austin, TX: R.G. Landes, Co. pp. 89–104, (1998).

Hook, V. et al., "Carboxypeptidase and Aminopeptidase Proteases in Pro–neuropeptide Processing," In: Hook, V.Y.H., ed., *Proteolytic and Cellular Mechanisms in Prohormone and Proprotein Processing,* Austin, TX: R.G. Landes Co. pp. 121–139, (1998).

Howland, D. et al., "Mutant and Native Human β–Amyloid Precursor Proteins in Transgenic Mouse Brain," *Neurobiology of Aging,* 16(4):685–699 (1995).

Hwang, S. et al., "Identification of Carboxypeptidase H Transcripts by Antisense RNA," *Mol. Brain Res.,* 25:135–139, (1994).

Hwang, S. et al., "Molecular Cloning Reveals Isoforms of Bovine $\alpha_1$–antichymotrypsin," *Proc. Natl. Acad. Sci. USA,* 91:9579–9583, (1994).

Hwang, S. et al., "Molecular Cloning of an Isoform of Phenol Sulforansferase from Human Brain Hippocampus," *Biochem. Biophys. Res. Commun.,* 207(2):701–707, (1995).

Hwang, S. et al., "Unique Reactive Site Domains of Neuroendocrine Isoforms of $Alpha_1$–Antichymotrypsin from Bovine Adrenal Medulla and Pituitary Revealed by Molecular Cloning," *FEBS Lett,* 368:471–476, (1995).

Hwang, S. et al., "High Level Expression and Characterization of Recombinant Human Hippocampus Phenol Sulfotransferase: A Novel Phenol–Sulfating Form of Phenol Sulfotransferase," *Protein Expression Purif.,* 11:125–134, (1997).

Hwang, S. et al., "Neuroendocrine $\alpha_1$–antichymotypsin as a possible Regulator of Prohormone and Neuropeptide Precursor Processing," In: Hook, V.Y.H., ed., *Proteolytic and Cellular Mechanisms in Prohormone and Proprotein Processing,* Austin, TX:R.G. Landes, pp. 159–171, (1998).

Ida, N. et al., "Rapid Cellular Uptake of Alzheimer Amyloid Ba4 Peptide by Cultured Human Neuroblastoma Cells," *FEBS Letters,* 394:174–178 (1996).

Johnson–Wood, K. et al., "Amyloid Precursor Protein Processing and $A\beta_{42}$ Deposition in a Transgenic Mouse Model of Alzheimer Disease," *Proc. Natl. Acad. Sci. USA,* 94:1550–1555, (1997).

Kelly, J. et al., "Amyloid B–peptide Disrupts Carbchol–induced Muscarinic Cholinergic Signal Transduction in Cortical Neurons," *Proc. Natl. Acad. Sci. USA,* 93:6753–6758 (1996).

Klafki, H.W. et al., "The Carboxyl Termini of β–Amyloid Peptides 1–40 and 1–42 Are Generated by Distinct γ–Secretase Activities," *J. Biol. Chem.,* 271(45):28655–28659 (1996).

Kounnas, M. et al., "LDL Receptor–Related Protein, a Multifunctional ApoE Receptor, Binds Secreted β–Amyloid Precursor Protein and Mediates Its Degradation," *Cell.,* 82:331–340 (1995).

Kreiger, T. et al., "Purification and Characterization of a Novel Thiol Protease Involved in Processing the Enkephalin Precursor," *J. Biol. Chem.,* 266(13):8376–8383, (1991).

Krieger, T. et al., "Prohormone Thiol Protease and Enkephalin Precursor Processing: Cleavage at Dibasic and Monobasic Sites," *J. Neurochem,* 59(1):26–31, (1992).

Krieger, T.et al., "Purification and Characterization of a Cathepsin D Protease from Bovine Chromaffin Granules," *Biochem.,* 31:4223–4231, (1992).

Laslop, A. et al., "Identification of Two Glycoproteins of Chromaffin Granules as the Carboxypeptidase H," *Neurosci. Lett,* 72:300–304, (1986).

LeBlanc, A. et al., "Processing of Amyloid Precursor Protein in Human Primary Neuron and Astrocyte Cultures," *J. Of Neurochem.,* 68(3):1183–1190, (1997).

Lee, R. et al., "Metabotropic Glutamate Receptors Increase Amyloid Precursor Protein Processing in Astrocytes: Inhibition by Cyclic AMP," *J. Of Neurochem.,* 68(5):1830–1835 (1997).

Lemere, C. et al., "The E280a Presenilin 1 Alzheimer Mutation Produces Increased Aβ42 Deposition and Severe Cerebellar Pathology," *Nature Medicine,* 2(10):1146–1150, (1996).

Li, Q. et al., "Proteolytic Processing of Alzheimer's Disease βA4 Amyloid Precursor Protein in Human Platelets," *The American Soc. For Biochem. And Molecular Biology Inc.,* 270(23):14140–14147, (1995).

Lieb, K. et al., "Interleukin–1β and Tumor Necrosis Factor–α Induce Expression of $\alpha_1$–Antichymotrypsin in Human Astrocytoma Cells by Activation of Nuclear Factor–κB," *J. Of Neurochem.,* 67(5):2039–2044 (1996).

Little, S. et al., "Zyme, a Novel and Potentially Amyloidogenic Enzyme cDNA Isolated from Alzheimer's Disease Brain," *J. Of Biological Chemistry,* 272(40):25135–25142, (1997).

Marx, J., "Dissecting How Presenilins Function–and Malfunction," *Science,* 274:1838–1840, (1996).

Meckelein, B. et al., "Human Endopeptidase (THOP1) Is Localized on Chromosome 19 Within the Linkage Region for the Late–Onset Alzheimer Disease AD2 Locus," *Genomics,* 31:246–249 (1996).

Moechars, D. et al., "Expression in Brain of Amyloid Precursor Protein Mutated in the A–secretase Site Causes Disturbed Behavior, Neuronal Degeneration and Premature Death in Transgenic Mice," *EMBO Journal,* 15(6):1265–1274 (1996).

Mok,S. et al., "A Novel Metalloprotease in Rat Brain Cleaves the Amyloid Precursor Protein of Alzheimer's Disease Generating Amyloidogenic Fragments," *Biochemistry,* 36(1):156–163, (1997).

Nelson, R. et al., "Clipsin, a Chymotrypsin–like Protease in Rat Brain Which Is Irreversibly Inhibited by α–1–Antichymotrypsin," *J. Of Biol. Chem.,* 265(7):3836–3843 (1990).

Nelson, R. et al., "Identification of a Chymotrypsin–like Mast Cell Protease in Rat Brain Capable of Generating the N–terminus of the Alzheimer Amyloid B–protein," *J. Of Neurochem.,* 61(2):567–577, (1993).

Papastoitsis, G. et al., "Identification of a Metalloprotease from Alzheimer's Disease Brain Able to Degrade the B–amyloid Precursor Protein and Generate Amyloidogenic Fragments," *Biochemistry,* 33(1):192–199, (1994).

Perez, R. et al., "Enhanced Release of Amyloid β–Protein from Condon 670/671 "Swedish" Mutant β–Amyloid Precursor Protein Occurs in Both Secretory and Endocytic Pathways," *J. Of Biol. Chem.,* 271(15):9100–9107 (1996).

Petryniak, M. et al., "Elevated Intracellular Calcium Concentration Increases Secretory Processing of the Amyloid Precursor Protein by a Tyrosine Phosphorylation–dependent Mechanism," *J. Biochem.,* 320:957–963 (1996).

Price, D. et al., "Amyloid Beta Amyloidosis in Alzheimer's Disease," *Current Opinion in Neurology,* 8:268–274 (1995).

Qiu, W. et al., "Degradation of Amyloid B–protein by a Metalloprotease Secreted by Microglia and Other Neural and Non–neural Cells," *J. Of Biol. Chem.,* 272(10):6641–6646 (1997).

Racchi, M. et al., "Secretory Processing of Amyloid Precursor Protein is Inhibited by Increase in Cellular Cholesterol Content," *J. Biochem.,* 322:893–898 (1997).

Reaume, A. et al., "Enhanced Amyloidogenic Processing of the β–Amyloid Precursor Protein in Gene–targeted Mice Bearing the Swedish Familial Alzheimer's Disease Mutations and a Humanized Aβ Sequence," *J. Of Biol. Chem.,* 271(38):23380–23388 (1996).

Reisine, T. et al., "Multireceptor–induced Release of Adrenocorticotropin from Anterior Pituitary Tumor Cells," *Biochem. Biophys. Res. Commun.,* 108:1251–1257, (1982).

Reisine, T. et al., "Activation of $B_2$–adrenergic Receptors on Mouse Anterior Pituitary Tumor Cells Increases Cyclic Adenosine 3':5'–monophosatesynthesis and Adrenocorticotropin Release," *J. Neurosci.,* 3(4):725–732, (1984).

Robakis, N. et al., "Biological Function and Processing of App.," In: Iqbal K, Motimer JA, Winblad B, Wisniewski HM, eds., *Research advances in Alzheimer's Disease and Related Disorders,* John Wiley & Sons, Ltd. pp. 685–692, (1995).

Rubin, H. et al., "Cloning, Expression, Purification, and Biological Activity of Recombinant Native and Variant Human α1–Antichymotrypsins," *The J. Of Biological Chemistry,* 265(2):1199–1207, (1990).

Saftig, P. et al., "Amyloidogenic Processing of Human Amyloid Precursor Protein in Hippocampal Neurons Devoid of Cathepsin D," *J. Of Biol. Chem.,* 271(44):27241–27244, (1996).

Schiller, M. et. al., "'Prohormone Thiol Protease' (Ptp) Processing of Recombinant Proenkephalin," *Biochem.,* 34:7988–7995, (1995).

Schiller, M. et al., "Expression of Recombinant Pro––neuropeptide Y, Proopiomelanocortin, and Proenkephalin: Relative Processing by 'Prohormone Thiol Protease' (PTP)," *FEBS Lett,* 382:6–10, (1996).

Schönlein, C. et al., "Purification And Characterization of A Novel metalloprotease From Human Brain With The Ability To Cleave Substrates Derived From The N–Terminus Of β–Amyloid Protein," *Biochem. Biophys. Res. Comm.,* 201(1):45–53, (1994).

Schubert, D., "Serpins Inhibit the Toxicity of Amyloid Peptides," *European Journal of Neuroscience,* 9:770–777, (1997).

Schwarzenbrunner, U. et al., "Sympathetic Axons and Nerve Terminals: the Protein Compositionof Small and Large Dense–core and of a Third Type of Vesicles," *Neurosci.,* 37(3):819–827, (1990).

Seubert, P. et al., "Secretion of B–amyloid Precursor Protein Cleaved at the Amino Terminus of the B–amyloid Peptide," *Nature,* 361:260–263, (1993).

Shinoda, M. et al., "Specific Inhibitor for Prolyl Endopeptidase Suppresses the Generation of Amyloid β Protein in NG108–15 Cells," *Biochem. Biophys. Res. Comm.,* 235(3):641–645, (1997).

Simons, M. et al., "Amyloidogenic Processing of the Human Amyloid Precursor Protein in Primary Cultures of Rat Hippocampal Neurons," *J. Of Neuroscience,* 16(3):899–908, (1996).

Sisodia, S. et al., "Role of the β–amyloid protein in Alzheimer's Disease," *FASEB Journal,* 9:366–370, (1995).

Stephens, D. et al., "Metabolites of the β–Amyloid Precursor Protein Generated by β–Secretase Localise to the Trans––Golgi Network and Late Endosome in 293 Cells," *J. Of Neuroscience Res.,* 46:211–225, (1996).

Suzuki, T. et al., "Phosphorylation of Alzheimer β–Amyloid Precursor–like Proteins," *Biochemistry,* 36:4643–4649, (1997).

Tezapsidis, N. et al., "Stimulation of 'Prohormone Thiol Protease' (Ptp) and [Met]enkephalin for Forskolin: Blockade of Elevated [Met]enkephalin by Cysteine Protease Inhibitor of Ptp," *J. Biol. Chem.,* 270(22):13285–13290, (1995).

Tezapsidis, N. et al., "Release of Nontransmembrane Full––length Alzheimer's Amyloid Precursor Protein from the Lumenar Surface of Chromaffin Granule Membranes," *Biochem.,* 37:1274–1282, (1998).

Thinakaran, G. et al., "Metabolism of the "Swedish" Amyloid Precursor Protein Variant in Neuro2a (N2a) Cells," *J. Of Biol. Chem.,* 271(16):9390–9397, (1996).

Tischer, E. et al., "β–Amyloid Precursor Protein, Location of Transmembrane Domain and Specificity of ,–Secretase Cleavage," *J. Of Biol. Chem.,* 271(36):21914–21919, (1996).

Tjernberg, L. et al., "Generation of Alzheimer Amyloid β Peptide through Nonspecific Proteolysis," *J. Of Biol. Chem.,* 272(3):1870–1875, (1997).

Toomim, C. et al., "Thiol and Aspartyl Proteolytic Activities in Secretory Vesicles of Bovine Pituitary," *Biochem. Biophys. Res. Commun.,* 18(2):449–455, (1992).

Toide, K. et al., "A Novel Prolyl Endopeptidase Inhibitor, Jtp–4819, with Potential for Treating Alzheimer's Disease," *Behavioural Brain Research,* 83:147–151, (1997).

Turner, R. et al., "Amyloids $\beta_{40}$ and $\beta_{42}$ Are Generated Intracellularly in Cultured Human Neurons and Their Secretion Increases with Maturation," *J. Of Biol. Chem.,* 271(15):8966–8970, (1996).

Vassilacopoulou, D. et al., "Full–length and Truncated Alzheimer Amyloid Precursors in Chromaffin Granules: Solubilization of Membrane Amyloid Precursor Is Mediated by an Enzymatic Mechanism," *J. Neurochem.,* 64:2140–2146, (1995).

Wang, R. et al., "The Profile of Soluble Amyloid β Protein in Cultured Cell Media," *J. Of Biol. Chem.,* 271(50):31894–31902, (1996).

Waters, S. et al., "Alterations of Peptide Metabolism and Neuropeptidase Activity in Senile Dementia of the Alzheimer's Type[a]," *Ann NY Acad. Sci.,* 814:30–39, (1997).

Wolozin, B. et al., "Differential Expression of Carboxyl Terminal Derivatives of Amyloid Precursor Protein Among Cell Lines," *J. Of Neurosci. Res.,* 33:163–169, (1992).

Yasothornsrikul, S. et al., "Arginine and Lysine Aminopeptidase Activities in Chromafin Granules of Bovine Adrenal Medulla: Relevance to Prohormone Processing," *J. Neurochem.,* 70:153–163, (1998).

Zhao, J. et al., "β–Secretase Processing of the β–Amyloid Precursor Protein in Transgenic Mice Is Efficient in Neurons but Inefficient in Astrocytes," *J. Of Biol. Chem.,* 271(49):31407–31411, (1996).

\* cited by examiner

SECRETASES RELATED TO ALZHEIMER'S DEMENTIA

This application is a continuation-in-part of application Ser. No. 09/173,887, filed Oct. 16, 1998, now U.S. Pat. No. 6,245,884, which is incorporated herein by reference.

This invention was made with government support under grant number NS24553 awarded by the National Institutes of Neurological Disease and Stroke. The government has certain rights in the invention.

BACKGROUND OF THE INVENTION

1. Field of the Invention

The present invention relates generally to medicine. More specifically, the invention is directed to methods relating to treating or preventing dementia.

2. Background Information

Dementia is a neurological disease that results in loss of intellectual capacity and is associated with widespread reduction in the number of nerve cells and brain tissue shrinkage. Memory is the mental capacity most often affected. The memory loss may first manifest itself in simple absentmindedness, a tendency to forget or misplace things, or to repeat oneself in conversation. As the dementia progresses, the loss of memory broadens in scope until the patient can no longer remember basic social and survival skills and function independently. Dementia can also result in a decline in the patient's language skills, spatial or temporal orientation, judgment, or other cognitive capacities. Dementia tends to run an insidious and progressive course.

Dementia results from a wide variety of distinctive pathological processes. The most common pathological process to cause dementia is Alzheimer's disease, which results in Alzheimer's-type dementia (AD). The second most common cause is multi-infarct, or vascular dementia, which results from hypertension or other vascular conditions. Dementia can also result from infectious disease, such as in Creutzfeldt-Jakob disease. Dementia occurs in Huntington's disease, which is caused by an autosomal dominant gene mutation, and in Parkinson's disease, which is associated with a motor disorder. Dementia also occurs from head injury and tumors.

Rare before age 50, AD affects nearly half of all people past the age of 85, which is the most rapidly growing portion of the United States population. As such, the current 4 million AD patients in the United States are expected to increase to about 14 million by the middle of the next century.

No method of preventing AD is known and treatment is primarily supportive, such as that provided by a family member in attendance. Stimulated memory exercises on a regular basis have been shown to slow, but not stop, memory loss. A few drugs, such as tacrine, result in a modest temporary improvement of cognition but do not stop the progression of dementia.

A hallmark of AD is the accumulation in brain of extracellular insoluble deposits called amyloid plaques, and abnormal lesions within neuronal cells called neurofibrillary tangles. The presence of amyloid plaques, together with neurofibrillary tangles, are the basis for definitive pathological diagnosis of AD. Increased plaque formation is associated with increased risk of AD.

The major components of amyloid plaques are the amyloid β-peptides, also called Aβ peptides, which consist of three proteins having 40, 42 or 43 amino acids, designated as the $A\beta_{1-40}$, $A\beta_{1-42}$, and $A\beta_{1-43}$ peptides. The amino acid sequences of the Aβ peptides are known and the sequence of the $A\beta_{1-42}$ is identical to that of the $A\beta_{1-40}$ peptide, except that the $A\beta_{1-42}$ peptide contains two additional amino acids at its carboxyl (COOH) terminus. Similarly, the amino acid sequence of the $A\beta_{1-43}$ peptide is identical to that of the $A\beta_{1-42}$ peptide except that the $A\beta_{1-43}$ peptide contains one additional amino acid at its carboxyl terminus. The Aβ peptides are thought to cause the nerve cell destruction in AD, in part, because they are toxic to neurons in vitro and in vivo.

The Aβ peptides are derived from larger amyloid precursor proteins (APP proteins), which consist of four proteins, designated as the $APP_{695}$, $APP_{714}$, $APP_{751}$, and $APP_{771}$ proteins, which contain 695, 714, 751 or 771 amino acids, respectively. The different APP proteins result from alternative ribonucleic acid splicing of a single APP gene product. The amino acid sequences of the APP proteins are also known and each APP protein contains the amino acid sequences of the Aβ peptides.

Proteases are believed to produce the Aβ peptides by recognizing and cleaving specific amino acid sequences within the APP proteins at or near the ends of the Aβ peptides. Such sequence specific proteases are thought to exist because they are necessary to produce from the APP proteins the $A\beta_{1-40}$, $A\beta_{1-42}$, and Aβ1-43 peptides consistently found in plaques.

But the proteases have not been isolated. Nonetheless, they have been named "secretases" because the Aβ peptides which they produce are secreted by cells into the extracellular environment. Moreover, the secretases have been named according to the cleavages that must occur to produce the Aβ peptides. The secretase that cleaves the amino terminal end of the Aβ peptides is called the β-secretase and that which cleaves the carboxyl terminal end of the Aβ peptides is called the γ-secretase. The γ-secretase determines whether the $A\beta_{1-40}$, $A\beta_{1-42}$, or $A\beta_{1-43}$ peptide is produced (see FIG. 1). But since the secretases have not been isolated, the terms β-secretase and γ-secretase each could relate to one or several protease species.

In addition to the Aβ peptides, proteolytic cleavage of another specific amino acid sequence within the APP proteins is known to occur and to produce α-APP and 10 kilodalton (kDa) fragments. That amino acid sequence lies within the Aβ peptide amino acid sequence of the APP proteins. Like the β-secretase and the γ-secretase, the protease responsible for that cleavage has also not been isolated but has been named the α-secretase (see FIG. 1). Significantly, the products produced by the α-secretase cleavage, the α-APP and the 10 kilodalton (kDa) fragments, do not form senile plaques.

Proteases can be isolated from tissue homogenates or lysed cell samples, but those samples can contain the proteases from cell organelles in which the product is not produced, but which may be able to cleave in vitro the precursor protein to produce the product. Thus, a problem in using such samples to isolate the secretases has been that proteases which produce the Aβ peptide in vitro, but not in vivo, may be erroneously isolated.

The problem can be avoided by isolating the secretase from cell organelles in which the APP proteins are processed in vivo. A cell organelle thought to be a site in which such processing occurs is the secretory vesicles of brain neuronal cells. But methods have not been developed to obtain sufficient amounts of pure secretory vesicles from neuronal cells to assay for secretase activity in those vesicles.

Large amounts of pure secretory vesicles can be obtained from chromaffin cells, neuroendocrine cells of the adrenal medulla, and have been used to obtain proteases. For example, carboxypeptidase H (CPH), prohormone thiol protease (PTP), and the prohormone convertases (PC1 and PC2), which process precursor proteins into peptides having opiate activity have been obtained from such vesicles. But chromaffin cells have not been shown to produce the Aβ peptides or have secretase activity.

The β-secretase, γ-secretase, and α-secretase must be isolated to understand how the neurotoxic Aβ peptides are produced so that AD can be prevented or treated. To isolate the secretase, new methods are needed for assaying the proteolytic activity of secretases in substantially purified preparations of the cell organelles in which the APP protein is processed in vivo. Moreover, new screening methods for selecting agents that affect the proteolytic activity of the secretases are needed to develop new pharmaceuticals for treating or preventing AD. Further, such new methods need to be applied and the secretases isolated.

The invention satisfies these needs by providing new methods of determining the proteolytic activity of secretases and isolating secretases having that activity. The invention also provides new screening methods for selecting agents that affect the activity of such secretases. Moreover, the invention discloses novel β-secretases obtained by such methods as well as methods of selecting agents inhibiting production of Aβ peptides by inhibiting the activity of those β-secretases.

SUMMARY OF THE INVENTION

The invention is directed to various novel β-secretases. One such β-secretase contains a protein having a molecular weight of about 61, 81 or 88 kDa as determined by cleavage of an APP substrate in a non-reducing SDS-PAGE in gel activity assay. In one embodiment, the β-secretase contains a protein that cleaves the APP substrate in the β-secretase recognition site at the Lys-Met bond.

Another is a protease complex having a molecular weight between about 180 and 200 kiloDaltons (kDa) as determined by Sephacryl chromatography that cleaves an APP substrate. In one embodiment, the protease complex cleaves the APP substrate in the β-secretase recognition site at the Lys-Met bond. In another embodiment, the protease complex contains proteins having molecular weights of about 66, 60, 33 and 29 kDa as determined by a reducing SDS-PAGE in gel protein staining assay. In another embodiment, the protease complex containis proteins having molecular weights of about 61, 81 and 88 kDa as determined by cleavage of an APP substrate in a non-reducing SDS-PAGE in gel activity assay.

Another β-secretase has a molecular weight between about 50 and 90 kDA as determined by Sephacryl chromatography and cleaves an APP substrate. In one embodiment, that β-secretase cleaves the APP substrate in the β-secretase recognition site at the Met-Asp bond. In another embodiment, the β-secretase contains 2 proteins having different electronegative charges as determined by ion exchange chromatography.

The invention is also directed to a method of selecting an agent that inhibits cleavage of the APP substrate by the β-secretases described above. The invention is further directed to a method of inhibiting production of an Aβ peptide by a cell or by an Alzheimer's disease patient using such a selected agent.

DETAILED DESCRIPTION OF THE INVENTION

Figure 1:
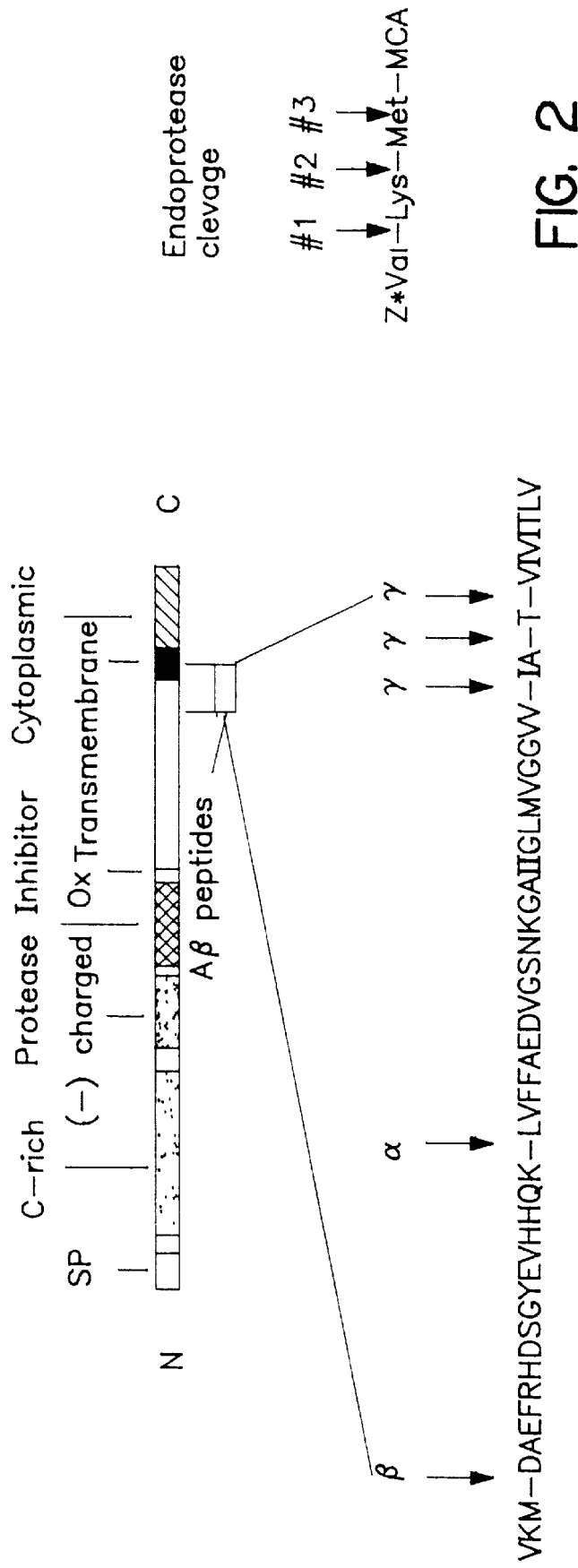
FIG. 1. The upper bar is a diagram of an amyloid precursor protein (APP protein). The amino and carboxyl termini of the APP protein are indicated by the letters "N" and "C," respectively. The relative location of various known regions within the APP protein are indicated, including the signal peptide (SP), cysteine-rich (C-rich), negatively charged ((−)charged), protease inhibitor, Ox antigen (Ox), transmembrane, cytoplasmic and Aβ peptide regions. The amino acid sequence of the Aβ peptides and regions flanking the Aβ peptides is shown by the letters below the amyloid precursor protein (SEQ ID NO.:1). Each letter represents an amino acid according to the conventional single letter amino acid abbreviation format. Scissile bonds within the amino acid sequence cleaved by the β-, γ-, or α-secretases are indicated by the β, γ, and α labels. Three scissile bonds cleaved by β-secretases which, in combination with scissile bond cleaved by the γ-secretase, produce the $A\beta_{1-40}$, $A\beta_{1-42}$, or $A\beta_{1-43}$ peptide. The three parallel lines below the amino acid sequence identify the amino acid sequences of the $A\beta_{1-40}$, $A\beta_{1-42}$, and $A\beta_{1-43}$ peptides.

This invention provides an assay for the proteolytic activity of secretases, particularly the β-secretase and the γ-secretase that produce the Aβ peptides found in the plaques of AD patients. The method is novel because the activity is detected in a substantially purified preparation of vesicles in which APP protein processing occurs in vivo. Based on that activity assay, new methods are disclosed to isolate the secretases from such substantially purified preparations. Isolating the secretases from the cell organelles in which the APP protein is processed insures that the secretases are the in vivo secretases and not merely a protease from a cell organelle in which such processing does not occur, but which is capable of cleaving the APP protein in vitro. The invention further provides methods of selecting an agent that affects the proteolytic activity of the substantially purified vesicles, the isolated secretase, or the cells containing the vesicles.

As discussed in Examples V and VII below, the secretory vesicles of chromaffin cells of the adrenal medulla, herein called "chromaffin vesicles," were discovered to contain Aβ peptides, specifically the $A\beta_{1-40}$ and the $A\beta_{1-42}$ peptides, and that chromaffin cells can secrete these peptides. As such, the chromaffin vesicles were found to contain the in vivo product produced by APP protein processing. Moreover, the vesicles were known to contain the APP proteins and presenilin 1 protein, a protein that affects secretase activity (see Vassilacopoulou et al., *J. Neurochem.* 64:2140–2146, (1995); Tezapsidis et al., *Biochem.* 37(5):1274–1282, (1998); Borchelt et al., *Neuron* 17:1005–1013, (1996); St. George-Hyslop et al., *Science* 264:1336–1340, (1994); Alzheimer's Disease Collaborative Group, *Nature Genet.* 11:219–222, (1995); and Wasco et al., *Nature Med.* 1:848, (1995)).

Chromaffin vesicles can be obtained in relatively large quantities. That capability, combined with the discovery that the chromaffin vesicles contained the Aβ peptides, permitted for the first time assaying a substantially pure preparation of cell organelles in which APP processing occurs for the proteolytic activity of a secretase. Further, chromaffin vesicles can be obtained in amounts which also permit isolating and sequencing the secretases present in those cell organelles.

As described more fully below in Examples I through XV, bovine chromaffin vesicles were initially discovered to have secretase proteolytic activity. Moreover, it was found that secretases having that activity could be isolated from bovine chromaffin vesicles. But the same methods can be applied to other mammalian species, including humans. As such, secretases from various mammalian species can be assayed for and isolated using the methods disclosed herein.

Further, the amino acid sequence of a bovine secretase is likely to be highly homologous with that of the corresponding human secretase because other bovine proteases are known to have a high degree of homology with the corresponding human protease. For example, the amino acid sequence of the bovine carboxypeptidase H is about 96% homologous with the corresponding human carboxypeptidase H (Hook et al., *Nature*, 295:341–342, (1982); Fricker et al., *Nature*, 323:461–464, (1986); and Manser et al., *Biochem. J.*, 267:517–525, (1990)). Once the amino acid sequence of a secretase from one species is obtained, the corresponding secretase in other species thus can be obtained using recombinant methods such as those described below.

The term "secretase" as used herein means a protease that cleaves an APP protein in vivo. A protease is a protein that enzymatically breaks a peptide bond between two amino acids or an amino acid and chemical moiety as described below. Although the term secretase implies the production of a soluble, secreted peptide, an APP derived product produced by a secretase of the invention need not necessarily be soluble or secreted. "Secretase" includes those secretases referred to as β-secretase and γ-secretase, each of which can relate to one or more protease species that produce the Aβ peptides. "Secretase" also includes the secretase referred to as α-secretase which can relate to one or more protease species that produce the α-APP fragment or the 10 kDa fragment.

The term "vesicles" as used herein refers to secretory vesicles and condensing vacuoles of the secretory pathway. Such vesicles have a membrane that forms a spherical shaped structure and that separates the contents of the vesicles from the rest of the cell. The vesicles process and store their contents until such time as the contents are secreted into the extracellular environment by a cellular process called exocytosis, which occurs by fusion of the secretory vesicle membrane with the cell membrane. The secretion can occur in response to a triggering event in the cell such as a hormone binding to a receptor. Vesicles can be identified by their characteristic morphology or by the presence of a chemical compound characteristic of such vesicles.

As used herein, the term "substantially pure" as used in regard to vesicles means that at least about 80% of the cell organelles in a sample are vesicles. Usually a substantially pure sample has about 95% or more vesicles and often has about 99% or more vesicles. Substantially pure vesicles include a single isolated vesicle. Substantially pure chromaffin vesicles result after approximately an 8-fold purification from the cell homogenate as described below in Example II.

Methods of Determining the Proteolytic Activity of a Secretase

One aspect of the invention is an assay for determining the proteolytic activity of a secretase by obtaining substantially pure vesicles, permeabilizing the vesicles, and incubating the permeablized vesicles with an APP substrate in conditions which allow the secretase to cleave the APP substrate. The cleavage of the APP substrate is detected and the activity of the secretase is thereby determined.

The vesicles can be obtained from any cell that contains vesicles in which APP protein processing occurs. Vesicles in which such processing occurs can be assayed for by the presence of an Aβ peptide, an α-APP fragment or a 10 kDa fragment in the vesicles using methods described below. Cells containing such vesicles include, for example, neuronal cells from brain tissue, chromaffin cells from adrenal medulla tissue, and platelets from blood. Tissue samples containing such cells can be surgically removed or platelets can be isolated from blood by means known in the art. For tissue samples, the vesicles can be obtained from mechanically homogenized tissue or from tissue disassociated by incubation with collagenase and DNAse (see, for example, Krieger et al., *Biochemistry*, 31, 4223–4231, (1992); Hook et al., *J. Biol. Chem.*, 260:5991–5997, (1985); and Tezapsidis et al., *J. Biol. Chem.*, 270:13285–13290, (1995), which are incorporated herein by reference).

The substantially pure vesicles can be obtained from the tissue homogenates or lysed cells using known methods (see *Current Protocols in Protein Science*, Vol. 1 and 2, Coligan et al., Ed., John Wiley and Sons, Pub., Chapter 4, pp. 4.0.1–4.3.21, (1997)). For example, substantially pure secretory vesicles can be isolated using discontinuous sucrose gradient centrifugation methods (see Krieger et al., ibid.; and Yasothornsrikul et al., *J. Neurochem.* 70, 153–163, (1998)). Vesicles also can be isolated using metrizamide gradient centrifugation (Toomin et al., *Biochem. Biophys. Res. Commun.*, 183:449–455, (1992); and Loh et al., *J. Biol. Chem.*, 259:8238–8245, (1984), or percoll gradient centrifugation (Russell, *Anal. Biochem.*, 113:229–238, (1981). If desired, capillary electrophoresis methods can be used to isolate individual vesicles (Chie et al, *Science*, 279:1190–1193, (1998)). Other methods, including differential centrifugation, fluorescence-activated sorting of organelles, immunoabsorption isolation, elutriation centrifugation, gel filtration, magnetic affinity chromatography, protein chromatographic resins, agarose gel electrophoresis, and free flow electrophoresis methods, also can be used to obtain substantially pure vesicles. The references cited in this paragraph are incorporated by reference.

The purity of the secretory vesicle preparation can be assayed for by morphological or chemical means. For example, vesicles can be identified by their characteristic morphology as observed by electron microscopy. The vesicles can be prepared for electron microscopy using various methods including ultra-thin sectioning and freeze-fracture methods. Vesicles also can be identified by the presence of a characteristic neurotransmitter or hormone present in such vesicles such as the (Met)enkephalin, catecholamines, chromogranins, neuropeptide Y, vasoactive intestinal peptide, somatostatin, and galanin found in chromaffin vesicles (Hook and Eiden, *FEBS Lett.* 172:212–218, (1984); Loh et al., *J. Biol. Chem.* 259:8238–8245, (1984); Yasothornsrikul et al., *J. Neurochem.* 70:153–163, (1998), which are incorporated herein by reference). The presence of the characteristic chemical compound can be determined by various means including, for example, by radioactive, fluorescent, cytochemical, immunological assays, or mass spectrometry methods. More specifically, such assays include radioimmunoassays, western blots or MALDI mass spectrometry. In addition, vesicles can be assayed using light and electron microscopic methods, fluorescent cell activated cell sorter methods, density gradient fractionation methods, immunoabsorption methods, or biochemical methods.

The activity of the secretases can be preserved while the vesicles are purified using known methods. For example, the vesicles can be obtained at a low temperature (e.g. 4° C.) and frozen (e.g. −70° C.) prior to assaying for secretase activity. The activity can also be preserved by obtaining the vesicles in the presence of a stabilizing agent known to preserve protease activity (see *Enzymes*, Dixon et al., Eds., Academic Press, Pub., pp. 11–12, (1979), and *Current Protocols in Protein Science*, Vol. 1 and 2, Coligan et al., Ed., John Wiley and Sons, Pub., Chapter 4, pp. 4.5.1–4.5.36, (1997), which are incorporated herein by reference). Known stabilizing agents include proteins, detergents and salts, such as albumin protein, CHAPS, EDTA, glycerol, and NaCl. Reducing agents are also known to preserve protein function and can be used (see Voet et al., *Biochemistry*, John Wiley and Sons, Pub., pp. 382–388 and 750–755, (1990), which is incorporated herein by reference). Known reducing agents include, for example, β-mercaptoethanol, DTT, and reduced glutathione (see Example VIII).

So that secretases within the vesicles are accessible to an APP substrate in an incubation solution, the vesicles are permeablized (see Voet et al., *Biochemistry*, John Wiley and Sons, Pub., pp. 284–288, (1990); and Krieger et al., ibid., which are incorporated herein by reference). Permeabilizing can result in a continuum of affects on the vesicle ranging from the formation of one or more holes in the membrane to complete lysis of the membrane. Vesicles can be permeablized, for example, by contact with a detergent or a disruptive agent such as CHAPS, sodium dodecyl sulfate, sodium cholate, digitonin, Brij 30 or TRITON X-100. Vesicles can be lysed, for example, by freeze-thawing, especially in a potassium chloride solution, by suspension in a hypoosmotic solution or by mechanical means such as sonication.

The permeablized vesicles are incubated with an APP substrate under appropriate conditions for cleavage of the APP substrate by a secretase. Various incubation conditions are known to affect protease cleavage. For example, the pH of the interior of chromaffin vesicles is acidic and some proteases in those vesicles are known to only function in an acidic incubation solution (Pollard et al., *J. Biol. Chem.* 254:1170–1177, (1979); and Hook et al., *FASEB J.* 8:1269–1278, (1994)). Thus, a condition for cleavage of the APP substrate includes an incubation solution having a pH of about 7.0 or less. But secretases in vesicles are released by cells into the extracellular environment, which can have a neutral or basic pH. Thus, vesicles can contain secretases that function at the neutral or basic pH of the extracellular environment and, as such, that pH can also be an appropriate condition. The pH of the incubation solution can be adjusted using known buffers (see Voet et al., *Biochemistry*, John Wiley and Sons, Pub., pp. 35–39, (1990)). Such buffers include, for example, citric acid, sodium phosphate, MES, HEPES and Tris-HCl buffers. The pH of the incubation solution can be determined using known methods such as, pH color indicators in liquid or paper formats, or pH meters. Examples III, IV, VIII, and IX show that the pH of the incubation solution can affect the activity of secretases.

Other conditions that affect the cleavage include the incubation temperature and incubation time. Proteolytic activity is a function of temperature with excessively low or high temperatures resulting in no detectable activity. An incubation temperature thus is any temperature which allows detection of a cleaved APP substrate. Usually an incubation temperature of about 30° to 45° C., with a typical temperature of about 35° to 40° C., and often a temperature of about 37° C. is used. Although not required, a constant temperature during the incubation time is preferred and can be achieved using an incubator, water bath or other known means. An insufficient or excessive incubation time results in too little production or too much degradation of the product to be detected. The incubation time for cleavage of an APP substrate is that amount of time which allows cleavage of the APP substrate to be detected. A preferred incubation time allows the cleavage of an APP substrate to go to completion, for example, in about 2 to 8 hours.

The proteolytic activity of a secretase is determined by the cleavage of an APP substrate. An "APP substrate" as used herein is a compound having a stereochemical structure that is the same as, or a mimic of, an amino acid sequence in an APP protein, an Aβ peptide, an α-APP fragment or a 10 kDa fragment recognized by a secretase. Thus, an APP substrate for detecting a β- or γ-secretase includes, for example, the APP$_{695}$, APP$_{714}$, APP$_{751}$, and APP$_{771}$ proteins and an APP substrate for detecting an α-secretase includes, for example, those proteins and the Aβ peptides. As discussed above, such proteins, peptides and fragments have been isolated and characterized (Kang et al., *Nature* 325:733–736, (1987); Kitaguchi et al., *Nature* 331:530–532, (1988); Ponte et al., *Nature* 331:525–527, (1988); Tanzi et al., *Nature* 331, 528–530, (1988); Tanzi et al., *Science* 235:880–884, (1987), Glenner et al., *Biochem. Biophys. Res. Commun.* 120, 885–890, (1984); Masters et al., *Proc. Natl. Acad. Sci. USA* 82: 4245–4249, (1985); Selkoe et al., *J. Neurochem.* 146: 1820–1834, (1986); Selkoe, *J. Biol. Chem.* 271:18295–18298, (1996); Mann et al., *Amer. J. Pathology* 148: 1257–66, (1996); Masters et al., *Proc. Natl. Acad. Sci. USA* 82: 4245–4249, (1985); Selkoe et al., *J. Neurochem.* 146: 1820–1834, (1986); Selkoe, *J. Biol. Chem.* 271:18295–18298, (1996); and Mann et al., *Amer. J. Pathology* 148: 1257–66, (1996)).

Such APP substrates can be produced by various methods known in the art (Knops et al., *J. Biol. Chem.* 266:7285–7290, (1991); Hines et al., *Cell. Molec. Biol. Res.* 40:273–284, (1994)). For example, the APP proteins can be made using recombinant technology and cloning the cDNA that encodes the proteins into a suitable expression system. An APP protein cDNA can be obtained, for example, by screening a human brain cDNA library with a DNA probe consisting of an oligonucleotide complementary to the APP protein cDNA, a PCR-generated DNA fragment of the APP protein cDNA, or a DNA fragment of the APP protein cDNA from an expressed sequence tagged (EST) database. Expression systems to produce APP proteins include, for example, *E. coli.*, baculovirus-infected insect cells, yeast cells, and mammalian cells. Alternatively, such proteins can be produced using in vitro methods, which transcribe and translate the RNA that encodes these proteins to produce the proteins. An APP so produced can be purified using methods such as described herein or otherwise known in the art.

An APP substrate is also known as an APP substrate-fusion substrate, in which a protein or peptide is attached to an APP substrate for the purpose of facilitating the isolation of the APP substrate. Proteins or polypeptides that facilitate purification include, for example, maltose-binding protein and multi-histidine polypeptides attached to the amino or carboxyl terminal end of the APP substrate. Thus, an example of an APP-fusion substrate is a multi-histidine polypeptide attached to the carboxyl terminus of an APP$_{695}$, APP$_{714}$, APP$_{751}$, or APP$_{771}$ protein. Such APP-fusion substrates can be produced using known methods such as by expression of the cDNA that encodes the APP-fusion substrate in a suitable expression system or in vitro translation of the encoding RNA. The APP-fusion substrates so produced can be purified by affinity binding to a column, such as by amylose, nickel or anti-APP antibody column chromatography.

Peptides are also known to function as protease substrates (see Sarath et al., Protease assay methods, In: *Proteolytic Enzymes, A Practical Approach*, R. J. Beynon and J. S. Bond, Eds., Oxford University Press, Pub., Chapter 3, pp 25–55, (1989). Often such a peptide substrate will contain the amino acids at a scissile bond in a precursor protein (see Benyon et al., *The Schecter and Berger Nomenclature for Protease Substrates, In: Proteolytic Enzymes, A Practical Approach*, R. J. Beynon and J. S. Bond, Eds., Oxford University Press, Pub., especially, Appendix 1, pp 231, (1989); and Barrett, *An Introduction to the Proteinases, In: Proteinase Inhibitors*, A. J. Barrett and G. Salvesen, Eds., Elsevier, Pub., Chapter 1, pp. 3–18, (1986)). A scissile bond is the peptide bond cleaved by a protease in a precursor protein. The amino acid on the amino terminal side of the scissile bond is often called the P1 amino acid and that on the carboxyl terminal side the P1' amino acid.

A protease that cleaves a scissile bond binds the P1 and P1' amino acids. For some proteases, the P1 amino acid is the primary determinant for protease binding to the precursor protein. For example, the protease trypsin is known to have a marked preference for binding basic P1 amino acids. Peptide substrates often contain the amino acids attached to the amino terminal side of a P1 amino acid because those amino acids can influence the determinant effect of the P1 amino acid.

An APP substrate also includes a peptide having an amino acid sequence recognized by a secretase containing a P1 or P1' amino acid, or both, of a scissile bond in an APP protein and one or more of the amino acids in the APP protein adjacent to either the P1 or P1' amino acids or both. For example, as shown in FIG. 1, a β-secretase scissile bond is between the P1 amino acid methionine (Met or M) and the P1' amino acid aspartic acid (Asp or A). A β-secretase recognition site thus includes, for example, a Met-Asp substrate.

Often an APP substrate is a peptide containing the P1 and P1' amino acids of a scissile bond in an APP protein and the one or two amino acids in the APP protein attached to the amino terminal side of the P1 amino acid. For example, as shown in FIG. 1, a lysine (Lys or K) is attached to the amino terminal side of the P1 amino acid of the β-secretase scissile bond and a valine (Val or V) is attached to the amino terminal side of the Lys. Thus, an APP substrate for the β-secretase includes the Lys-Met-Asp and Val-Lys-Met-Asp (SEQ. ID NO.:1) substrates.

The APP substrate peptide containing the P1 and P1' amino acids of a scissile bond in an APP protein can be determined for the γ-secretase and the α-secretase in the same manner. For example, as shown in FIG. 1, the γ-secretase scissile bond of the Aβ$_{1-40}$ peptide has a Val P1 amino acid, an isoleucine (Ile or I) P1' amino acid, a second Val attached to the amino terminal side of the P1 amino acid and a glycine (Gly or G) attached to the amino terminal side of the second Val. As such, the γ-secretase recognition site for the Aβ$_{1-40}$ peptide includes, for example, the Val-Ile, Val-Val-Ile and Gly-Val-Val-Ile (SEQ ID NO.:2) substrates. The γ-secretase recognition site for the Aβ$_{1-42}$ peptide thus includes, for example, the Ala-Thr, Ile-Ala-Thr and Val-Ile-Ala-Thr (SEQ ID NO.:3) substrates and that the g-secretase recognition site for the Aβ$_{1-43}$ peptide includes, for example, the Thr-Val, Ala-Thr-Val, and Ile-Ala-Thr-Val (SEQ ID NO.:4) sequences. Similarly, the α-secretase recognition site can be determined from the amino acids in the APP protein surrounding the α-secretase scissile bond.

Proteases are known to have endoprotease, aminopeptidase, or carboxypeptidase activity, or a combination of these activities (see Sarath et al., ibid.). A protease having endoprotease activity cleaves the peptide bond between two adjacent amino acids, neither of which is a terminal amino acid, or, as discussed below. between a non-terminal amino acid and a terminal blocking group. A protease having aminopeptidase activity only cleaves the peptide bond between the amino terminal amino acid and its adjacent amino acid. A protease having carboxypeptidase activity only cleaves the peptide bond between the carboxyl terminal amino acid and its adjacent amino acid.

Secretases of the invention also can have endoprotease, aminopeptidase, or carboxypeptidase activity, or a combination of these activities. For example, an Aβ peptide can be cleaved from an APP protein directly by endoprotease cleavage of the scissile bonds at both ends of the Aβ peptide. But an Aβ peptide also can be produced by an endoprotease cleavage of a scissile bond distal to the terminal amino acids of the Aβ peptide followed by aminopeptidase or carboxypeptidase cleavage of the amino acids flanking the terminal amino acids of the Aβ peptide.

An APP substrate often contains one or more amino terminal or carboxyl terminal blocking groups, which prevent aminopeptidase or carboxypeptidase cleavage, respectively (see Sarath et al., ibid.). But an amino terminal blocking group does not prevent carboxypeptidase and, conversely, a carboxyl terminal blocking group does not prevent aminopeptidase cleavage. As such, an APP substrate can often contain both an amino terminal and carboxy terminal blocking group to prevent both aminopeptidase and carboxylpeptidase cleavage. An APP substrate containing both blocking groups can only be cleaved, if at all, by a secretase having endoprotease activity.

Blocking groups and methods of making substrates containing blocking groups are known in the art (see, for example, Methods in Enzymology, Vol. 244, "Proteolytic Enzymes," A. J. Barrett, Ed., Chapters 46, 47, and 48, (1994); and Green and Wuts, Protective Groups in Organic Synthesis, John Wiley and Sons, Pub., (1991) which are herein incorporated by reference). Amino terminal blocking groups include, for example, acyl (Ac), benzoyl (Bz), succinyl (Suc), carbobenzoxy (Z), p-bromocarbobenzoxy, p-chlorocarbobenzoxy, p-methoxycarbobenzoxy, p-methoxyphenylazocarbobenzoxy, p-nitrocarbobenzoxy, p-phenylazocarbobenoxy, tert-butoxycarbonyl (Boc), benzoyl and the like. Carboxyl blocking groups include, for example, aminomethylcourmarinamide (MCA), the diazomethanes, the p-nitroanlide (pNA), pNA.Tosylate, 2-naphthylamine, the acyloxymethanes, including the (benzoyloxy)methanes, (alkyloxy)methanes, the N,O-diacyl hydroxamates, including the N-aminoacyl-O-4-nitrobenzoyl hydroxamates, esters, including methyl, ethyl and nitrophenyl esters, chloromethylketone and the like.

Although endoproteases do not cleave terminal amino acids, endoproteases can cleave a carboxyl terminal blocking group attached via a peptide bond to the carboxyl terminal amino acid of a peptide containing two or more amino acids (see Sarath et al., ibid.). If the carboxyl terminal amino acid is the P1 amino acid of a scissile bond in a precursor protein, the carboxyl terminal blocking group mimics the P1' amino acid in that scissile bond. Moreover, endoprotease cleavage of the carboxyl terminal blocking group mimics the cleavage of the corresponding scissile bond in the precursor protein. Such carboxyl terminal blocking groups include, for example, MCA, pNA, and pNA.Tosylate. An APP substrate which contains such a carboxyl terminal blocking group and an amino terminal blocking group can only be cleaved, if at all, by an endoprotease.

An APP substrate includes a secretase recognition site that contains a P1 amino acid of a scissile bond in an APP protein and a carboxyl terminal blocking group which replaces the P1' amino acid in that scissile bond. The APP substrate also contains one or more of the amino acids in the APP protein attached to the amino terminal side of the P1 amino acid. Such an APP substrate will bind a secretase which binds the corresponding scissile bond in the APP protein because the substrate contains the P1 amino acid, the primary determinant for that binding. For example, a β-secretase recognition site containing such a carboxyl terminal blocking group includes, for example, the Val-Lys-Met-MCA substrate in which the MCA group replaces the Asp P1' amino acid of the β-secretase scissile bond. Endoprotease cleavage of the Met-MCA peptide bond in that substrate is equivalent to endoprotease cleavage of the scissile bond Met-Asp of the β-secretase recognition site in the APP protein. Similarly a γ-secretase recognition site for the $A\beta_{1-40}$ peptide includes, for example, the Gly-Val-Val-pNA substrate in which the pNA group replaces the Ile P1' amino acid of the corresponding γ-secretase recognition site and endoprotease cleavage of the pNA group is equivalent to endoprotease cleavage of the corresponding scissile bond in the APP protein. Similar substrates are envisioned for the γ-secretase recognition site for the $A\beta_{1-42}$, and $A\beta_{1-43}$ peptides and the α-secretase recognition site.

The APP substrate as discussed in the paragraph above can also contain an amino terminal blocking group. Only those secretases having endoprotease activity will cleave that APP substrate and the endoprotease cleavage of the substrate will mimic that which occurs in the APP protein. Examples of such APP substrates include, but are not limited to, Z*Lys-Met-MCA, Z*Val-Lys-Met-MCA, Z*Val-Val-MCA, Z*Gly-Val-Val-MCA, Z*Ile-Ala-MCA, Z*Val-Ile-Ala-MCA, Z*Ala-Thr-MCA, and Z*Ile-Ala-Thr-MCA substrates. In these examples, Z represents the amino terminal blocking group carbobenzoxy and the star (*) indicates a non-peptide bond between the Z and the adjacent amino acid. The MCA represents the carboxyl terminal blocking group aminomethylcourmarinamide and the dashes (—) represent peptide bonds between the MCA and the adjacent amino acid or between adjacent amino acids.

Secretases having aminopeptidase activity can be assayed for using an APP substrate that contains an amino acid of a secretase recognition site and a carboxyl terminal blocking group. Examples of such APP substrates include Met-MCA and Lys-MCA substrates from the β-secretase recognition site. However, if such substrates contain only one amino acid, the substrate cannot be cleaved by an endoprotease because the only amino acid is an amino terminal amino acid. The Met-MCA and Lys-MCA substrates were used to identify β-secretase aminopeptidase secretase activities (see Example IV).

An APP substrate often contains one or more labels that facilitate detection of the substrate or the APP derived product. A label can be an atom or a chemical moiety. Substrates containing a label can be made by methods known in the art. For example, radioactive atoms such as $^3H$ or $^{32}P$ can be attached to an APP substrate to detect an APP derived product. Also, heavy atoms or atom clusters such as, gold clusters can be attached. Moreover, fluorescent molecules such as, fluorescein, rhodamine, or green fluorescent protein, can be attached. A label can have more than one function. For example, the MCA is a carboxyl blocking group that is not fluorescent when bound in an APP substrate, is an APP derived product when cleaved by an endoprotease from a substrate, and is a label because, when MCA is cleaved from the substrate, it becomes fluorescent aminomethylcourmarinamide (AMC or free MCA) which is detectable (Azaryan and Hook, Arch. Biochem. Biophys. 314:171–177, (1994); and Azaryan et al., J. Biol. Chem. 270:8201–8208, which are incorporated herein by reference).

Cleavage of an APP substrate can be detected by the presence of an APP derived product. The term "APP derived product" refers to a protein, polypeptide, peptide or chemical moiety produced by proteolytic cleavage of an APP substrate. An APP derived product includes, for example, an Aβ peptide, an α-APP fragment, a 10 kDa fragment, and AMC. A chemical moiety is the blocking group or label discussed above.

An APP derived product or an APP protein can be qualitatively or quantitatively detected using various methods. For example, these products or proteins can be detected by an immunoassay using antibodies such as monoclonal or polyclonal antibodies against the $A\beta_{1-40}$ peptide, $A\beta_{1-42}$ peptide, $A\beta_{1-43}$ peptide, the amino terminal or the carboxyl terminal regions of the APP proteins and the APP proteins. Such antibodies are commercially available, for example, from PENINSULA LABORATORIES, Belmont, Calif.; CALBIOCHEM, San Diego, Calif.; QCB, Hopkinton, Mass.; or IMMUNODYNAMICS, La Jolla, Calif.

SDS-PAGE electrophoresis and western blots can also be used to detect an APP derived product and an APP protein (see Example XII). Other methods include detecting a label on or from the APP derived product or APP protein such as a radioactive or fluorescent label. Microsequencing, amino acid composition analysis, or mass spectrometry analysis can also be used (see Example XV). Chromatography separation methods based on physical parameters such as molecular weight, charge, or hydrophobicity can be used. Preferred chromatography methods include high pressure liquid chromatography (HPLC) and automated liquid chromatography (FPLC, PHARMACIA, Piscataway, N.J.). Spectrophotometric detection methods such as UV absorbance at 280 nm or 210–215 nm, can also be used. Known light or electron microscopic methods as well as fluorescent activated cell sorter methods also can be used to detect APP derived products and APP proteins. The quantitative fluorescence analysis using a fluorometer was used to detect the fluorescent AMC product produced by β-secretase cleavage of the Z*Val-Lys-Met-MCA, Met-MCA, and Lys-MCA (see Examples III, IV, VIII, and IX).

Figure 2:
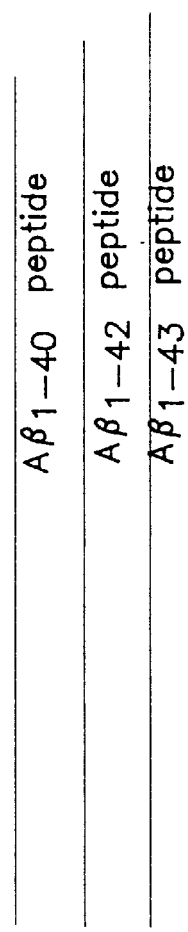
FIG. 2. The bonds, labeled #1, #2, and #3, in the Z*Val-Lys-Met-MCA substrate cleaved by a secretase having endoprotease activity are shown. The Z, Val, Lys, Met, and MCA in the substrate represent a carbobenzoxy, valine, lysine, methionine, and aminomethylcourmarinamide group, respectively. The star (*) and dash (—) represent nonpeptide and peptide bonds, respectively FIG. 3. The fluorescence activity is plotted as a function of the pH at which a lysate of substantially pure chromaffin vesicles is incubated with the Z*Val-Lys-Met-MCA substrate. The fluorescence activity is the relative fluorescence of the free MCA (AMC) released by proteolytic cleavage of the substrate.

FIG. 2 shows the endoprotease cleavages that can occur in an APP substrate containing a β-secretase recognition site and amino and carboxyl terminal blocking groups and how such cleavages can be detected. In that figure, the three endoprotease cleavages of the APP substrate Z*Val-Lys-Met-MCA are shown (#1, #2, and #3). The Met-MCA bond (#3) mimics the scissile bond between the P1 and P1' amino acids Met and Asp in the APP protein at the amino terminal end of the Aβ peptide. Endoprotease cleavage of the Met-MCA bond in the substrate is equivalent to endoprotease cleavage of the APP protein. That cleavage in the APP protein would produce directly the amino terminal end of the Aβ peptide. That cleavage can be detected by the characteristic fluorescence produced by AMC (free MCA).

Endoprotease cleavage of the Lys-Met bond (#2) and the Val-Lys bond (#3) in the Z*Val-Lys-Met-MCA substrate produces a Met-MCA and Lys-Met-MCA peptide, respectively. The corresponding endoprotease cleavages in the APP proteins would be distal to the amino terminal end of the Aβ peptide. However, such distal endoprotease cleavages can occur in vivo because, as discussed above, such cleavages followed by aminopeptidase cleavage of the flanking amino acids can produce the amino terminal end of the Aβ peptide.

The Met-MCA and Lys-Met-MCA peptides are not fluorescent, but contain free amino terminal amino acids, which an aminopeptidase can cleave to liberate AMC. To insure that the endoprotease cleavages of the Lys-Met and the Val-Lys bonds are detected, an aminopeptidase can be added to an incubation solution to liberate AMC from the Met-MCA and Lys-Met-MCA peptides. Known aminopeptidases include, for example, aminopeptidase M and methionine aminopeptidase (*Mammalian Proteases, a Glossary and Bibliography*, J. K. Mcdonald and A. J. Barrett, Ed., Academic Press, Pub., p. 23–99, (1986)). In this manner, all the endoprotease cleavages of the Z*Val-Lys-Met-MCA substrate can be detected.

Such methods were used to identify endoprotease activity of one or more β-secretases in substantially purified vesicles (see Examples III, VIII, and IX). In particular, a secretase in substantially purified vesicles was shown to cleave the Z*Val-Lys-Met-MCA substrate at a pH of about 4.0 to about 5.5 using these methods.

Methods of Isolating a Secretase

The present invention also is directed to a method of isolating a secretase using the assay described above to determine the proteolytic activity of a secretase and isolating that secretase from substantially purified vesicles. Generally, the isolation is done by assaying the activity of the secretase after each step in the isolation. If necessary, the activity can be preserved during the isolation procedure using methods such as those described above, including, for example isolating the secretase at a low temperature (e.g. 4° C.), or in the presence of one or more of the above-described reducing or stabilizing agents.

The secretase is isolated based on its physical properties. For example, a secretase can be isolated based on its molecular weight and size using gel filtration chromatography such as, Sephacryl S200, Sephadex G150, Superose 6 or 12, and Superdex 75 or 200 resin chromatography. A secretase can also be isolated based on its charge using ion-exchange chromatography such as DEAE-Sepharose, CM Sephadex, MonoQ, MonoS and MonoP resin chromatography. In addition, a secretase can be isolated based on its water solubility using hydrophobicity chromatography such as phenyl Sepharose, butyl Sepharose and octyl Sepharose resin chromatography. Interactions between the secretase and hydroxyapatite can also be used for isolation using, for example, macro-prep hydroxyapatite, and Bio-Gel HT hydroxyapatite resins.

A secretase can also be isolated based on specific biochemical properties of the secretase using affinity chromatography. For example, the secretase can be isolated using APP substrate affinity chromatography under conditions in which the secretase binds the APP substrate but does not cleave it. Glycosylated secretases can be isolated using lectin affinity chromatography such as, concanavalin A-Sepharose, lentil lectin Sepharose, wheat germ lectin Sepharose resin chromatography. The proteolytic activity of sulfhydryl groups such as those on cysteine amino acids can be used to isolate the secretases using thiol-propyl chromatography. Finally, the affinity of the secretases for specific dyes can be used for separation such as, blue-Sepharose resin chromatography. Other affinity chromatography methods include arginine-Sepharose, benzamidine Sepharose, glutathione Sepharose, lysine-Sepharose and chelating Sepharose resin chromatography. The secretases can also be isolated by non-chromatographic fractionation methods using, for example, native gel electrophoresis, analytical ultracentrifugation and differential ammonium sulfate precipitation methods (see Example XII).

Using such methods, alone or in combination, a secretase of the invention can be isolated. The term "isolated" when used in reference to a secretase means that the secretase is relatively free of other proteins, amino acids, lipids and other biological materials normally associated with a cell. Generally, an isolated secretase constitutes at least about 50%, and usually about 70% to 80%, and often about 90 to 95% or more of the biological material in a sample. A secretase often is isolated such that it is free of other substances that affect the cleavage of an APP substrate, such as an inhibitor or activator protein. The extent to which the secretases are isolated using such methods can be determined by known protein assays. For example, the amount of protein in the resulting chromatographic fractionation can be quantitated using the Lowry method and the specific activity can be used to quantitate the isolation (see Example XIII). Alternatively, SDS-PAGE or two-dimensional gel electrophoresis and mass spectroscopy methods can be used.

After initial isolation of a secretase, antibodies specific to the secretase can be produced and secretases isolated using immunoaffinity chromatography. Such antibodies can be produced using known immunological methods including, for example, monoclonal antibody and polyclonal antibody production methods (see Haylow and Lane, *Antibodies: A Laboratory Manual,* Cold Spring Harbor Laboratory Press, (1988)).

The amino acid sequence of the secretase also can be determined after isolation of the secretase. For example, the amino acid sequence of the secretase can be determined using peptide microsequencing methods known in the art (see "Current Protocals in Protein Science," Vol. 1 and 2, Coligan et al., Ed., (1997), John Wiley and Sons). Alternatively, the partial amino acid sequence can be determined from fragments of the secretase using mass spectrometry and Edman microsequencing methods ("*Current Protocols in Protein Science,*" Vol. 1 and 2, Coligan et al., Ed., (1997), John Wiley and Sons). For example, the secretase can be isolated using an SDS-PAGE gel and stained with coomassie blue in the gel. The secretase in the gel can be subjected to in-gel tryptic digestion and the amount of protein determined by amino acid analysis. Tryptic peptide fragments can be separated by HPLC, and the amino acid sequence of each fragment determined by Edman microsequencing and mass spectrometry methods. The amino acid sequence of the secretase can be determined from the amino acid sequences of the peptide fragments using computer analysis of known amino acid sequences.

Based on the partial amino acid sequence of a secretase, the cDNA of the secretase can be cloned (see, for example, *Molecular Cloning, a Laboratory Manual,* Vol. 1, 2, and 3, Sambrook et al., Ed., Cold Spring Harbor Laboratory Press, Pub., (1989); and *Current Protocols in Molecular Biology,* Vol. 1, 2, and 3, Ausubel et al., Ed., Wiley Interscience, Pub., (1997)). Briefly, partial, cloned secretase cDNAs are obtained by reverse transcription-polymerase chain reaction methods (RT-PCR) using oligonucleotides complementary to the partial amino acid secretase sequences. The complementary oligonucleotides synthetically synthesized can contain either degenerate codons, including inosine, or be optimized for mammalian cell use. The PCR-generated DNA fragment is analyzed for nucleic acid sequences and restriction enzyme sequences, and overlapping sequences among the different PCR-generated DNA fragments are determined. Northern blot or RT-PCR analysis using the PCR-generated cDNAs, or complementary oligonucleotides, so produced are used to determine tissues that produce mRNAs encoding the secretase. A cDNA library from such tissues is constructed and screened using the PCR-generated secretase cDNA or the complementary oligonucleotides. From such screened cDNA libraries, the cDNA sequence encoding the full-length amino acid sequence of the secretase is determined.

The cDNA of a secretase can also be obtained by generating antibodies against the partial amino acid sequences, screening cDNA expression libraries with an anti-secretase antibody, and analyzing the nucleic acid sequences of such clones. The amino acid sequence of the secretase can be deduced from the secretase cDNA sequence. The full-length cDNA can be cloned in an expression system such as in *E. coli,* Sf9 insect cells, yeast, or mammalian cell lines, and the activity of the expressed secretase determined to confirm that the cDNA encodes a functional secretase.

Another method of obtaining the cDNA of a secretase is to clone the secretase in a genetic screen for isolating the secretase cDNA using the bacteriophage l regulatory circuit, where the viral repressor is specifically cleaved to initiate the lytic phase of bacteriophage to allow detection and isolation of plaques containing the secretase cDNA(s) (Sices and Kristie, *Proc. Natl. Acad. Sci. USA* 95:2828–2833, (1988)).

The gene(s) encoding a secretase can be isolated by screening a genomic library with the cDNAs encoding the partial or full length secretase, or with the oligonucleotides that are complementary to a sequence encoding a determined secretase amino acid sequence. The nucleic acid sequence of the secretase genomic DNA is determined, and the exon/intron structure of the secretase gene is determined by comparing the DNA sequence of the gene to the nucleic acid sequence of the secretase cDNA.

Once the cDNA encoding a partial or full-length endogenous secretase is obtained from one animal species, that cDNA can be used to obtain endogenous secretases from another animal species using known methods (*Molecular Cloning, a Laboratory Manual,* ibid.; and *Current Protocols in Molecular Biology,* ibid.). For example, the cDNA encoding the partial bovine secretase can be used to obtain cDNAs encoding human secretases. Briefly, a partial or full-length bovine cDNA, or a labeled complementary oligonucleotide, is used to isolate the human secretase cDNA by screening human cDNA libraries constructed from tissues that contain secretase mRNA, determined by northern blot or RT-PCR analyses. Alternatively, the human secretase cDNA can be obtained by searching the expressed sequence tag database (EST) for human cDNA sequences similar to the bovine secretase cDNA. DNA sequencing of the resulting secretase clones can be performed to determine the nucleic acid sequence encoding the human secretase and the corresponding amino acid sequence can be deduced. The cDNA encoding the human secretase can be cloned in and expressed by a suitable expression vector and the activity of the expressed secretase can be determined. The genes encoding the human secretase can be cloned as described herein.

The nucleic acid sequence of a secretase can also be used to produce the secretase using known recombinant methods (*Molecular Cloning, a Laboratory Manual,* ibid.; and *Current Protocols in Molecular Biology,* ibid.). The cDNA encoding the secretase can be inserted into an appropriate expression vector and the expression vector introduced into an appropriate host as described herein. Expression of the secretase by the host is stimulated by expression of a vector promotor.

Methods of Screening for Agents that Affect the Proteolytic Activity of a Secretase Another aspect of the invention is a method of selecting an agent that alters the cleavage of an APP substrate by a secretase. Such agents, particularly those that decrease the cleavage by the β-secretase and γ-secretases or that increase the cleavage by the α-secretase, are useful for developing drugs that prevent or treat AD. Agents having divergent chemical structures can be assayed using such methods including, for example, small organic molecules that optionally contain heteroatoms or metals, amino acids, peptides, polypeptides, proteins, peptidomimetics, nucleic acids, carbohydrates, glycoproteins, lipids, and lipoproteins.

The method is based on comparing the APP substrate cleavage, or the APP protein, or APP derived product production that occurs with and without an agent. This is achieved by determining the APP substrate cleavage or the APP protein or the APP derived product produced in a first incubation or culture solution lacking the agent and comparing that result with that which occurs in a second incubation or culture solution containing the agent. The first and second incubation or culture solutions can be different solutions or the same solution to which the agent is added or removed. The APP substrate cleavage, the APP protein, and the APP derived product can be assayed using the methods described herein. The concentration of the agent can vary due to parameters known in the art such as the hydrophobicity, charge, size and potency of the agent, but typically is about a $10^{-9}$ to $10^{-3}$ M.

Agents are selected that alter the cleavage of an APP substrate or production of an APP protein or an APP derived product. The cleavage or production is altered if the agent causes a significant change in the cleavage or production relative to that which occurs without the agent. A significant change can be determined using a variety of qualitative or quantitative methods, such as, for example, by a visual or statistical analysis of the comparison data. For example, the mean amounts of an APP derived product obtained with and without the agent can be analyzed using a two-sided Student's t-test and a $p \geq 0.02$ or greater, and preferably a $p \geq 0.05$, in that test can be indicative of a significant difference.

Often agents are screened using substantially pure vesicles as the source of the secretase. But substantially pure vesicles can contain, in addition to secretases, other substances that affect the cleavage of an APP substrate, such as the presenilin 1 protein. Thus, a screen using such vesicles selects for agents that directly or indirectly alter the cleavage. An agent can directly affect the cleavage by, for example, inhibiting the binding of an APP substrate to a secretase. But an agent can also indirectly alter the cleavage by affecting an inhibitor or activator substance which in turn affects the activity of the secretase. For example, proteases may be present in the vesicle that produce the secretase from a precursor protein or that degrade the secretase. An agent thus can indirectly affect the secretase activity by affecting the proteases which produce or degrade the secretase. Often permeablized chromaffin vesicles and an APP protein, Aβ peptide, Z*Val-Lys-Met-MCA, Z*Gly-Val-Val-MCA, Z*Val-Ile-Ala-MCA, or Z*Ile-Ala-Thr-MCA substrate are used in the assay.

An isolated secretase, obtained as described above, can also be used to select for agents that affect the activity of the secretase. Using an isolated secretase free of other substances that affect the cleavage of an APP substrate, agents can be selected that directly affect cleavage of the APP substrate. The affect of an agent on such an isolated secretase and on substantially purified vesicles can be compared to determine the direct and indirect affects of the agent. Moreover, that comparison can be used to determine if the vesicles contain inhibitors or activators of the secretase removed during isolation of the secretase.

The protease class to which an isolated secretase belongs can be determined using agents known to selectively inhibit different classes of proteases. For example, E-64c, cystatin, and p-mercuribenzoate inhibit cysteine proteases; phenylmethylsulfonyl fluoride (PMSF), soybean trypsin inhibitor, and $\alpha_1$-antitrypsin inhibit serine proteases; ethylenediaminetetraacetic acid (EDTA) and 1,10-O-phenanthroline inhibit metalloproteases; and pepstatin A inhibits aspartyl proteases. (See Examples XI and XIV).

In another method, a cell containing vesicles having the proteolytic activity of a secretase is used to select for an agent. Cells containing such vesicles can be identified using the methods described above to determine the proteolytic activity of a secretase in the vesicles. The cells are cultured in a first culture solution without the agent and in a second culture solution with the agent and the production of an APP protein or an APP derived product by the cell, especially an Aβ peptide, α-APP fragment or 10 kDa fragment, in the first and second culture solution compared.

A problem with using transformed cell cultures or cell lines to select agents is that the agents may be ineffective in vivo because cells in culture can process a protein in a manner unrelated to that which occurs in vivo. Thus, agents that affect the processing of such cells are ineffective because the processing that they affect does not occur in vivo. The cell based method provided in the present invention avoids this problem by selecting cells determined to contain vesicles that have the proteolytic activity of a secretase. As such, the method insures that the cells process the APP protein in the cell organelle in which that processing occurs in vivo.

A cell used in this method can be obtained from a variety sources. For example, disassociated cells maintained in a primary culture can be used in the method. Such disassociated cells can be maintained in a primary culture using known methods (see, for example, Hook et al., ibid.; and Tezapsidis et al., ibid.). Disassociated cells have the advantage of retaining many of the functional characteristics that they have in the tissue that they are obtained from. But primary cultures of disassociated cells generally die after a period of time. Cell lines, transformed cells and cloned cells, on the other hand, have the advantage of being immortal. But such cells are known to often abnormally process proteins. As such, it is particularly important to use immortalized cells that are determined to contain vesicles in which the proteolytic activity of a secretase occurs so as to insure that the cells are processing the APP protein in the same manner as in vivo. Various cell transformation methods can be used to obtain such cells (see for example, Alarid et al. *Development,* 122(10):3319–29, (1996); and Schecter et al., *Neuroendocrinology,* 56(3):300–11, (1992), which are incorporated herein by reference). A chromaffin cell, either obtained by disassociation or by transformation, is often used in this method.

In the cell based assay of the present invention, the agent is often present when the cells are producing an APP derived product because some agents are known to only affect a protease in a cell when the protease is producing a product. For example, agents are known to inhibit enkephalin production in chromaffin cells only when the chromaffin cells are actively producing enkephalin (Tezapsidis et al., ibid.). Various methods can induce cells to produce proteolytically processed peptides in vesicles. For example, proteolytic processing can be induced by exocytosis. Exocytosis can be induced by various means including, for example, by increasing the extracellular potassium chloride concentration or by binding nicotinic cholinergic receptors on cells with nicotine. Proteolytic processing of the Aβ peptides can also be induced by stimulating protein kinase with phorbol esters (Koo, *Molec. Medicine,* 3:204–211, (1997); and LeBlanc et al., *J. Neurosci.,* 18:2908–2913, (1998)).

For example, as shown in Example VII, chromaffin cells can be induced to produce an Aβ peptide by culturing the cells in potassium chloride (about 5 to 500 mM), nicotine (about $10^{-3}$ to $10^{-6}$ M), or phorbol ester (about $10^{-3}$ to $10^{-6}$ M) for a sufficient amount of time to stimulate production (about 1 to 72 hours for the nicotine and potassium chloride and about 12 to 96 hours for the phorbol ester). During active production of the Aβ peptide by the cells, an agent is incubated with the chromaffin cells under appropriate conditions and for an appropriate amount of time (e.g. about 2 to 8 hours). The cells can then be lysed and the production of an Aβ peptide with and without the agent compared. To facilitate that comparison, a protease inhibitor such as, chymostatin, leupeptin, and soybean trypsin inhibitor (STI), can be added when cells are lysed to prevent non-specific digestion of the Aβ peptide by non-specific proteases released by cell lysis.

The cell based assay can be used to select an agent that affects cell expression. For example, the expression of a nucleic acid that encodes a secretase can be tested in such an assay. Inhibitors of gene transcription, such as actinomycin D or an antisense nucleic acid, or agents that modify protein transcription factors that regulate gene expression, such as steroids, also can be tested. The cell based assay can also be used to select agents that affect protein processing, including those affecting RNA splicing, RNA polyadenylation, RNA editing, protein translation, signal peptidase processing, protein folding including chaperone-mediated folding, disulfide bond formation, glycosylation, phosphorylation, covalent modification including methylation, prenylation, and acylation, and association with endogenous protein factors that modify secretase activity.

Agents found to alter cleavage of an APP substrate can be evaluated in vivo using transgenic AD animal models. Transgenic animal models have been developed in which the animals have brain amyloid plaques containing Aβ peptides and, in some models, exhibit cognitive deficits such as excessive memory loss. Exemplary transgenic animals include mice that contain the Indiana mutation of the human APP cDNA under the control of the PDGF promoter (Johnson-Wood et al., *Proc. Natl. Acad. Sci., USA,* 94:1550–1555, (1997)). These mice express increased levels of brain Aβ peptides and amyloid plaques and show cognitive deficits. Another exemplary transgenic animal is a mouse strain containing the Swedish mutation of the human APP-695 cDNA with the hamster PrP promoter (Hsiao, *J. Neural Transmission,* 49:135–144, (1997)). These mice express increased levels of brain Aβ peptides, have amyloid plaques and are memory impaired.

Agents can be administered to such animals using methods known in the art, particularly those methods that result in the agent traversing the blood brain barrier. For example, such agents can be administered by direct injection into the central nervous system or by administration with a minipump. Agents that naturally traverse the blood brain barrier can be systematically administered by intravenous, subcutaneous, or oral routes. Such agents can be administered in effective doses which for example can range from 0.001 to 10 mg/kg body weight. Agents can be administered prophylactically or therapeutically in single or multiple dose schedules.

Agents can be assayed by histopathological examination of the brains from such transgenic animals. For example, quantitative, microscopic analysis of amyloid plaque formation can be used to determine the effect of the agent. Agents which reduce the size or frequency of amyloid plaques are preferred. In addition, agents can be assayed by measuring brain levels of $A\beta_{1-40}$, $A\beta_{1-42}$, or $A\beta_{1-43}$ by radioimmunoassay or ELISA. Agents that reduce $A\beta_{1-40}$, $A\beta_{1-42}$, or $A\beta_{1-43}$ levels are preferred. Agents also can be assayed for their effect on the cognitive behavior of such animals using known methods. For example, the memory capability of mice can be determined using the water maize test. Agents which enhance the memory capability are preferred.

Agents that effectively reduce or inhibit Aβ peptide production or amyloid plaque formation or increase memory in any of the methods described above can be used to treat or prevent AD. Persons identified as probable AD patients by known medical methods can be administered such agents. Also, people diagnosed as having a high probability of developing AD can be administered such agents. Patients are assessed for improvement in cognitive abilities. Upon autopsy, brain tissue is assessed for amyloid plaques and Aβ levels. Agents are administered by known methods such as those described above for the animal model.

Agents that effectively reduce or inhibit Aβ peptide production or amyloid plaque formation or increase memory can also be used to enhance memory function of people, especially the elderly. People can be administered such agents and assayed for improved memory capability. Agents can be administered by known methods such as those described above for the in vivo assay.

The following examples are intended to illustrate but not limit the present invention.

EXAMPLE I

Isolation of Chromaffin Vesicles

Chromaffin vesicles were isolated from fresh bovine adrenal medulla by discontinuous sucrose gradient centrifugation (Krieger et al., *Biochemistry,* 31, 4223–4231, (1992); Yasothornsrikul et al., *J. Neurochem.* 70, 153–163, (1998)). Briefly, fresh bovine adrenal glands were dissected to obtain the medulla region. These medulla from 40 glands were homogenized in 200–250 ml ice-cold 0.32 M sucrose, and the homogenate was centrifuged at 1,500 rpm in a GSA rotor (Sorvall centrifuge) for 20 minutes at 4° C.

The resultant supernatant was collected and centrifuged at 8,800 rpm in a GSA rotor (Sorvall centrifuge) for 20 minutes at 4° C. to obtain a pellet of chromaffin vesicles. The pellet of chromaffin vesicles was washed three times in 0.32 M sucrose. Each wash consisted of resuspending the pellet of chromaffin vesicles with an equal volume (same volume as original homogenate) of 0.32 M sucrose and centrifugation at 8,800 rpm in a GSA rotor to collect the vesicles as the pellet.

After washing, the chromaffin vesicles were resuspended in 120 ml of 0.32 M sucrose and subjected to discontinuous sucrose gradient centrifugation. For that centrifugation, 10 ml of the washed chromaffin vesicle suspension was layered on top of 25 ml of 1.6 M sucrose in each of 12 centrifuge tubes. The 12 tubes of sucrose gradient were centrifuged in a SW28 rotor at 25,000 rpm for 120 minutes at 4° C. The pellets of isolated chromaffin vesicles from 12 tubes were resuspended in 12 ml of 0.015 M KCl with a glass-glass homogenizer, and stored at −70° C., prior to use. A chromaffin vesicle lysate was prepared by freeze-thawing the isolated chromaffin vesicles in the 15 mM KCl.

EXAMPLE II

Assay for Chromaffin Vesicles

The chromaffin vesicles in the Example I preparation were assayed for the chromaffin vesicle markers (Met) enkephalin, catecholamines, the lysosomal marker acid phosphatase and total protein. Fractions containing the highest amount of chromaffin vesicle markers were identified as chromaffin vesicles. The homogeneity of the chromaffin vesicles was approximately 99% as assayed by the proteolytic activity of the chromaffin vesicle markers (Met)

enkephalin and catecholamines and the absence of the lysosomal marker acid phosphatase. Electron microscopy showed that uniform, homogeneous, and intact chromaffin vesicles were isolated. The chromaffin vesicles were purified approximately 8-fold from the cell homogenate based on the measurement of the picograms of (Met)enkephalin per microgram of protein in the samples.

EXAMPLE III

β-secretase Endoprotease Activity

The APP substrate, Z*Val-Lys-Met-MCA, was used to identify a β-secretase based on endoprotease activity. That substrate was commercially obtained and had a purity of 99% or better as determined by the manufacturers (PENINSULA LABORATORIES, Belmont, Calif. and PHOENIX LABORATORIES, Mountain View, Calif.).

The β-secretase endoprotease activity was identified by incubating the chromaffin vesicle lysate (2–10 μl of 10–20 mg protein/ml) with the Z*Val-Lys-Met-MCA substrate (100 μM final concentration) and detecting AMC fluorescence. The chromaffin vesicle lysate was prepared as described in Example I. The endoprotease activity was determined as a function of pH by varying the pH of the incubation solution between 3.0 to 8.0 in 0.5 pH increments. Citric acid, sodium phosphate, and Tris-HCl buffers (100 mM final concentration) were used to adjust the pH of the incubation solutions between 3.0 to 5.5, 6.0 to 7.5, and 8.0, respectively. Duplicate samples at each pH increment (100 μl each) were distributed among 22 wells in a covered microtiter well plate and incubated at 37° C. for 8 hours in a water bath.

As discussed above, endoprotease cleavage between the Met-MCA bond in the Z*Val-Lys-Met-MCA substrate produces fluorescent AMC, but endoprotease cleavage between the Lys-Met or Val-Lys bonds in that substrate produces non-fluorescent Lys-Met-MCA and Met-MCA peptides. To insure that the latter two endoprotease cleavages were detected, aminopeptidase M (20 μg/ml final concentration, BOEHRINGER MANNHEIM) was added to each incubation solutions to produce fluorescent AMC from the Lys-Met-MCA and Met-MCA peptides. Prior to adding the aminopeptidase M, each incubation solution was adjusted to a pH 8.3 using Tris-HCl because aminopeptidase M functions at a basic pH. A second incubation at 37° C. for 1 hour in the water bath was conducted to complete the aminopeptidase M reaction.

Upon termination of that second incubation, AMC fluorescence was assayed using a fluorometer (IDEXX fluorometer, FCA Fluorescence Concentration Analyzer, cat. no. 10-105-2, BAXTER HEALTH CARE CORP., Mundelein, Ill.) at excitation and emission wavelengths of 365 and 450 nm, respectively. Standard AMC concentrations were also measured to quantitate relative fluorescence with the molar amount (pmol) of AMC generated by the secretase. The resulting AMC fluorescence reflects the endoprotease activity in cleaving either the Met-MCA, Lys-Met. and Val-Lys bonds in the Z*Val-Lys-Met-MCA substrate.

Figure 3:
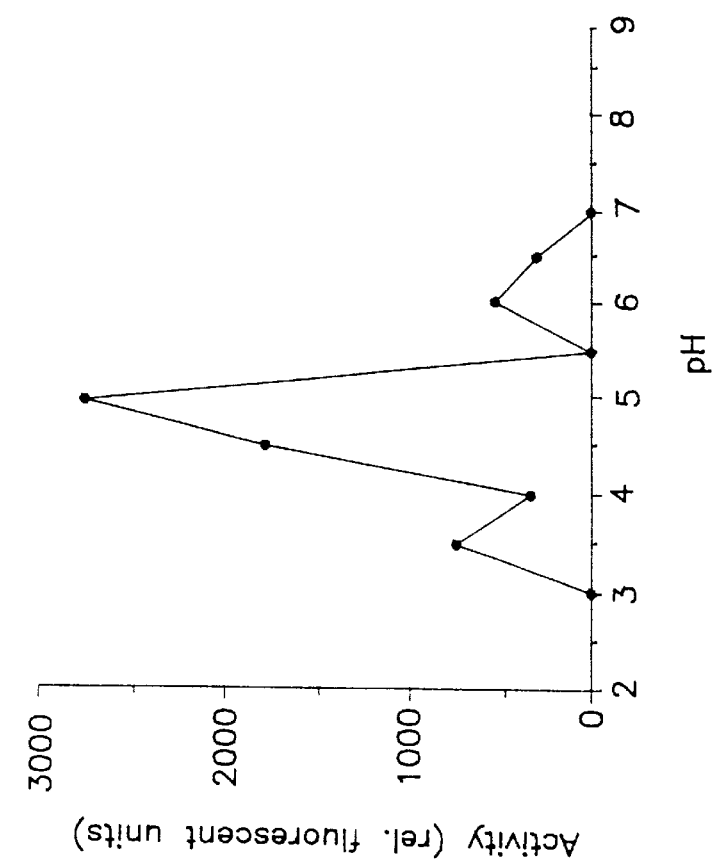

The AMC fluorescence was plotted as a function of pH and is shown in FIG. 3. Analysis of that plot shows a principal β-secretase endoprotease activity having a pH optimum of about 4.5–5.0. In addition, the plot shows two lesser β-secretase endoprotease activities having pH optimums of about pH 3.5 and 6.0–6.5.

EXAMPLE IV

β-secretase Aminopeptidase Activity

The APP substrates, Met-MCA, and Lys-MCA, were used to identify a β-secretase based on aminopeptidase activity. Those substrates were commercially obtained and had a purity of 99% or greater as determined by the manufacturers (PENINSULA LABORATORIES, Belmont, Calif. and PHOENIX LABORATORIES, Mountain View, Calif.).

The β-secretase Met aminopeptidase activity was identified by incubating the chromaffin vesicle lysate (5 μl of 10–15 mg/ml) with the Met-MCA substrate (100 μM final concentration) and detecting the resulting AMC fluorescence. The chromaffin vesicle lysate was prepared as described in Example I. The aminopeptidase activity was determined as function of pH by varying the pH of the incubation solution between 3.0 to 8.0 in 0.5 pH increments. Citric acid, sodium phosphate, and Tris-HCl buffers (100 mM final concentration) were used to adjust the pH of the incubation solutions between 3.0 to 5.5, 6.0 to 7.5, and 8.0, respectively. Duplicate samples at each pH increment (100 μl each) were distributed among 22 wells in a covered microtiter well plate and incubated at 37° C. for 4 hours in a humidified incubator.

Similarly, the μ-secretase Lys aminopeptidase activity was identified by incubating the chromaffin vesicle lysate (5 μl of 10–15 mg/ml) with the Lys-MCA substrate (100 μM final concentration) and detecting the resulting AMC fluorescence. The incubation was identical to that described for the Met aminopeptidase assay except that the incubation time was 2 hours long.

Upon termination of the incubations, AMC fluorescence was assayed as described above. The resulting AMC fluorescence indicating β-secretase Met and Lys aminopeptidase activities was plotted as a function of pH and is shown in FIGS. 4 and 5, respectively.

Figure 4:
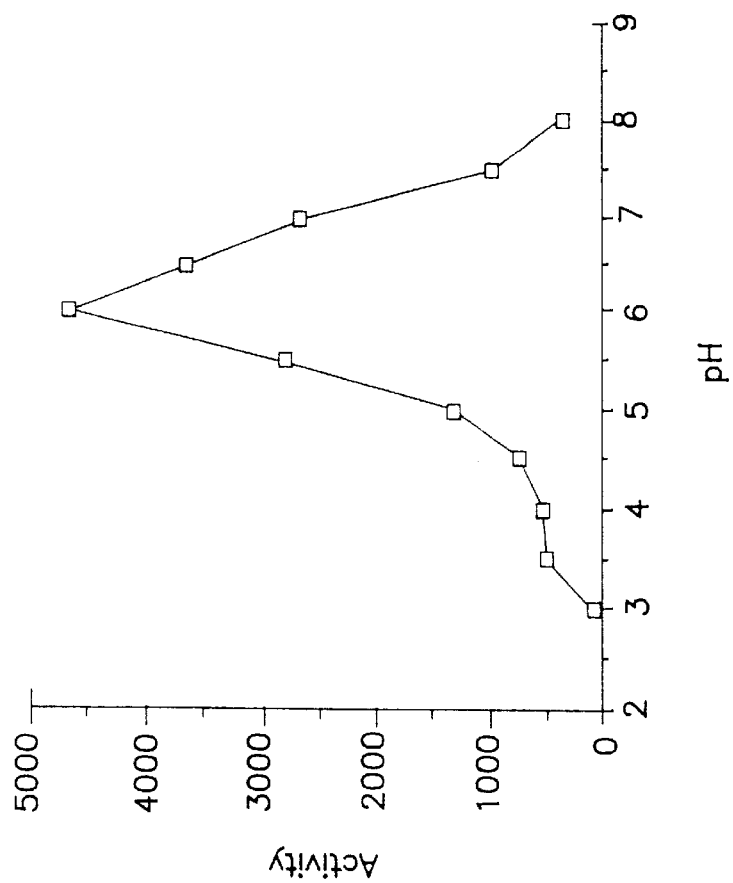
FIG. 4. The fluorescence activity is plotted as a function of the pH at which a lysate of substantially pure chromaffin vesicles is incubated with the Met-MCA substrate. The fluorescence activity is the relative fluorescence of the free MCA (AMC) released by proteolytic cleavage of the substrate.
Figure 5:
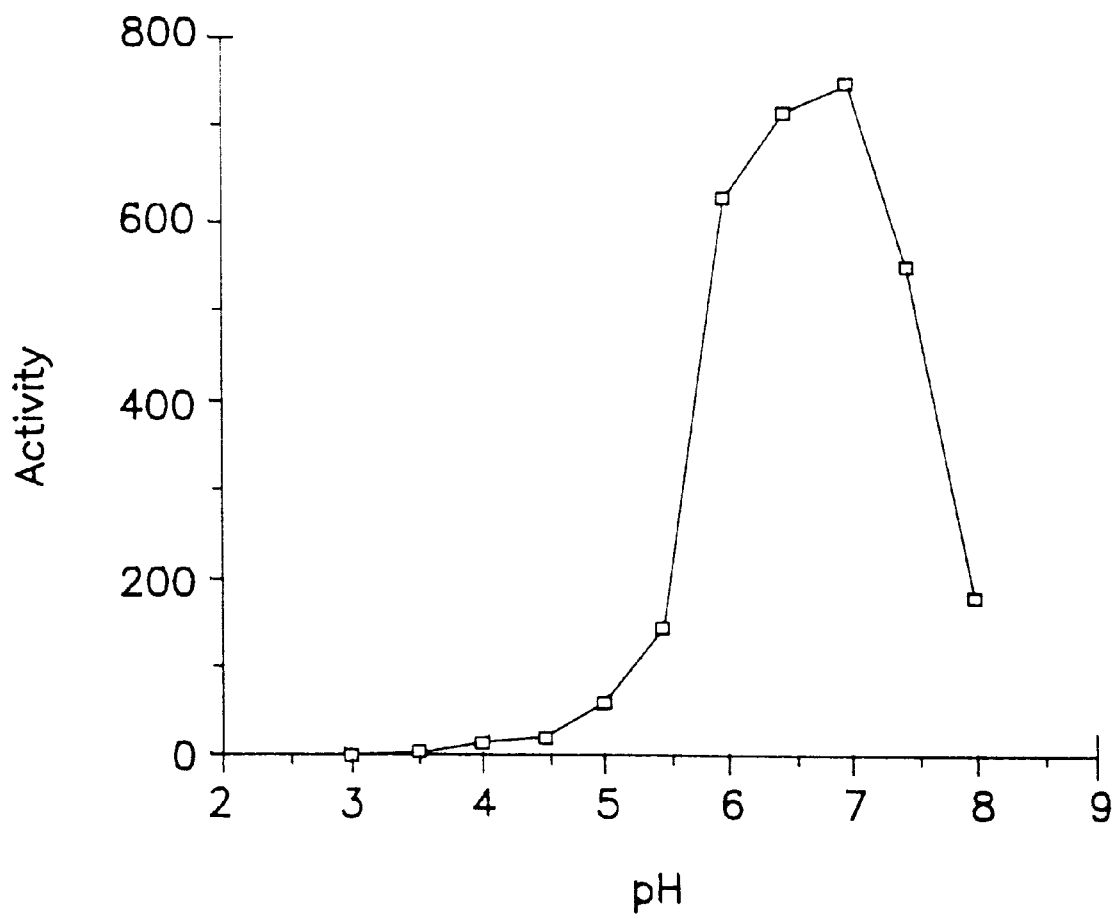
FIG. 5. The fluorescence activity is plotted as a function of the pH at which the lysate of substantially pure chromaffin vesicles is incubated with the Lys-MCA substrate. The fluorescence activity is the relative fluorescence of the free MCA (AMC) released by proteolytic cleavage of the substrate.

Analysis of FIG. 4 shows a β-secretase Met aminopeptidase activity having a pH optimum of about 5.5–6.5. Similarly, analysis of FIG. 5 shows a β-secretase Lys aminopeptidase activity having a pH optimum of about 6.0–7.0.

EXAMPLE V

Identification of Aβ peptides

The chromaffin vesicle lysate was analyzed for the proteolytic activity of Aβ peptides using commercially available polyclonal and monoclonal antibodies against the $A\beta_{1-40}$ and $A\beta_{1-42}$ (PENINSULA LABORATORIES, Belmont, Calif. and QCB, Hopinton, Mass., respectively) in known radioimmunoassay (RIA) and ELISA methods. The chromaffin vesicles contained $A\beta_{1-40}$ at 0.051 pg/ug protein as determined by RIA and a detectable amount of $A\beta_{1-42}$ as determined by ELISA.

EXAMPLE VI

APP Protein Distribution in Chromaffin Cells

The distribution of APP protein in chromaffin cells was determined using a monoclonal antibody directed against the amino terminal region of the APP protein (Anti-Alzheimer precursor protein A4, clone #22C11, BOEHRINGER MANNHEIM, Indianapolis, Ind.) in established immunofluorescent cytological methods. Fluorescent light microscopic analysis of chromaffin cells stained by this method showed that the APP protein was localized in the chromaffin vesicles and not in the cell nucleus.

EXAMPLE VII

Aβ-peptide Secretion by Chromaffin Cells

Primary chromaffin cell cultures containing approximately 2 million cells in each culture were produced using established methods (Hook et al., ibid.; and Tezapsidis et al., ibid.). Exocytosis of the contents of the vesicles in such cells was induced by exposing the cells to KCl (50 mM) or nicotine (10 μM) for 15 minutes. The media was removed from the cells and the $A\beta_{1-40}$ peptide in the media was determined using the RIA assay described in Example V. The KCl and nicotine exposure caused an approximately 350-fold and 550-fold increase in the concentration of $A\beta_{1-40}$ peptide in the media, respectively, relative to that of a control media from a culture identically processed but which did not receive KCL or nicotine. The results show that chromaffin cells exocytosis results in the secretion of Aβ peptide.

EXAMPLE VIII

Figure 6:
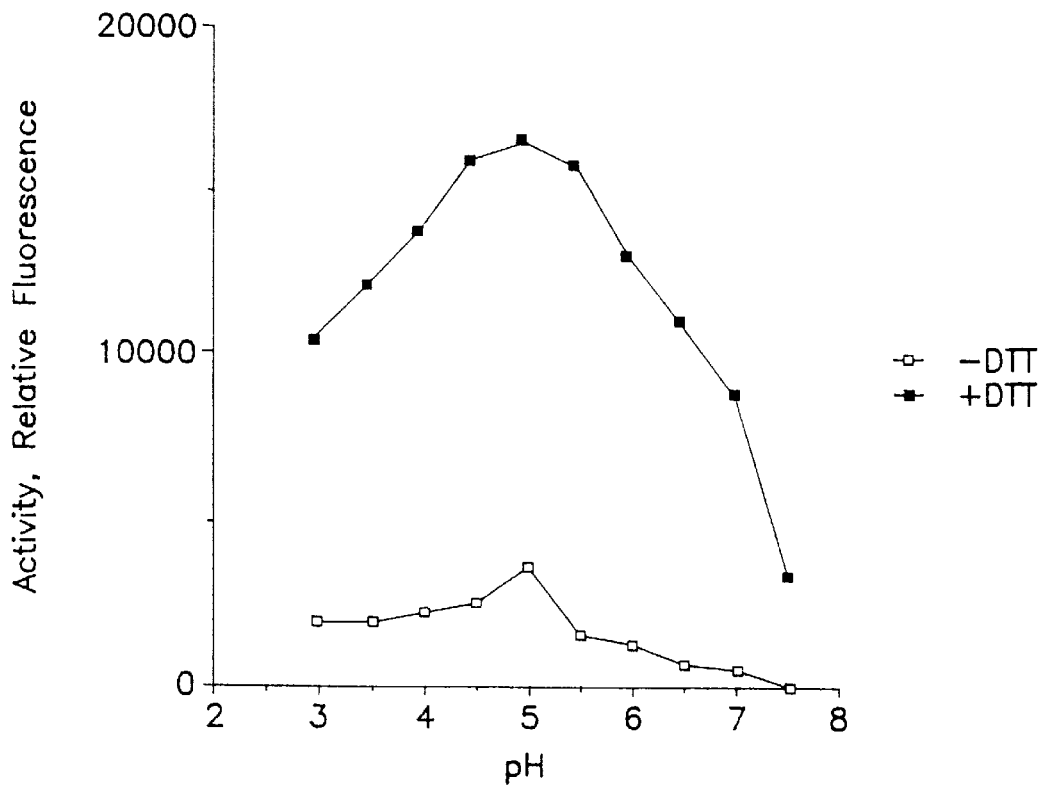
FIG. 6. The fluorescence activity is plotted as a function of the pH at which the lysate of substantially pure chromaffin vesicles is incubated with the Z*Val-Lys-Met-MCA substrate in the presence and absence of DTT (closed and open squares, respectively). The fluorescence activity is the relative fluorescence of the free MCA (AMC) released by proteolytic cleavage of the substrate.

Effect of Reducing Agents on β-secretase Endoprotease Activity in Chromaffin Vesicles The effect of the reducing agent dithiothreitol (DTT) on β-secretase endoprotease activity was determined using the assay described in Example III. Briefly, the lysed vesicles were incubated with the substrate Z*Val-Lys-Met-MCA in the presence or absence of 1 mM DTT and the resulting fluorescence plotted as a function of pH. Both with and without DTT, β-secretase endoprotease activity was detected and in both cases that activity had pH optimum of about 4.0 to 6.0, which is consistent with the intravesicular pH of chromaffin vesicles. But the DTT resulted in a significant increase in the β-secretase endoprotease activity, approximately 5-fold (see FIG. 6). These results show that DTT, although not essential, significantly increases β-secretase endoprotease activity.

EXAMPLE IX

Figure 7:
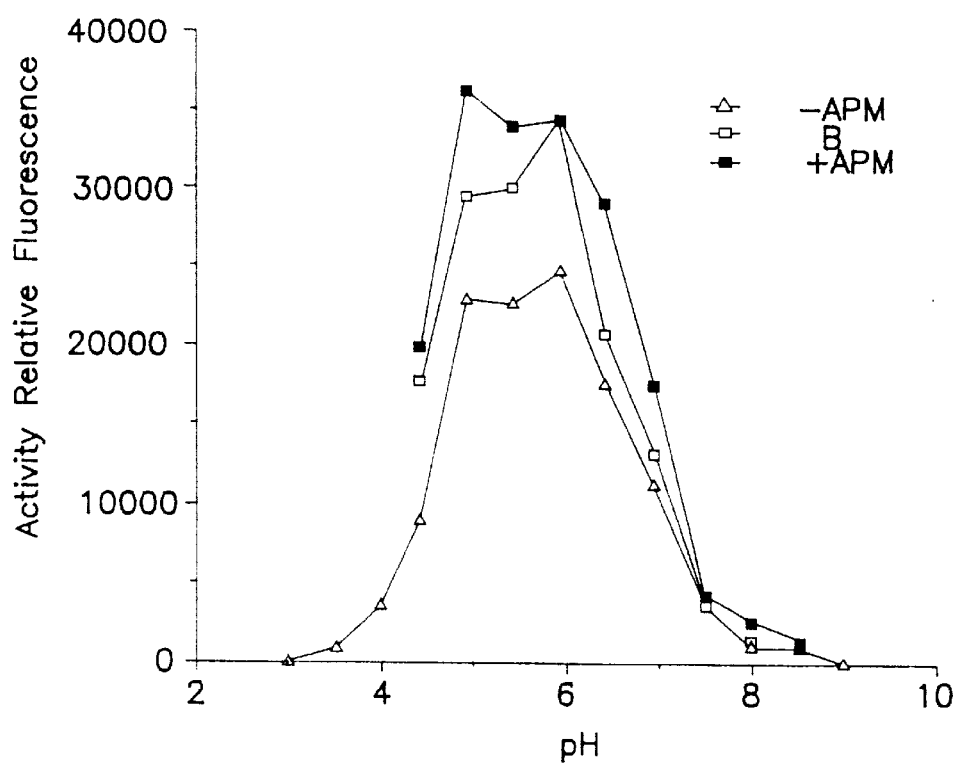
FIG. 7. The fluorescence activity is plotted as a function of the pH at which the lysate of substantially pure chromaffin vesicles is incubated with the Z*Val-Lys-Met-MCA substrate in the presence of DTT without aminopeptidase M (open triangles), with basic pH buffer (open squares), or with aminopeptidase M (closed squares). The fluorescence activity is the relative fluorescence of the free MCA (AMC) released by proteolytic cleavage of the substrate.

Effect of Aminopeptidase M on β-secretase Endoprotease Activity in Chromaffin Vesicles The effect of the aminopeptidase M and the basic pH buffer used in the β-secretase endoprotease activity assay was determined. The assay was conducted as described in Example VIII with DTT. Three assays were conducted, one with aminopeptidase M in its basic pH buffer, another with the basic pH buffer but not aminopeptidase M, and a third without either the buffer or the aminopeptidase M. Briefly, the chromaffin vesicle lysate and the substrate Z*Val-Lys-Met-MCA were incubated for 30 minutes at a specified pH and the resulting fluorescence measured. The aminopeptidase M in the basic pH buffer or that buffer alone (final concentration of 75 mM Tris-HCl pH 8.2) was added to the assay and incubated an additional 60 minutes at 37° C. The resulting fluorescence was plotted as a function of pH, which showed that β-secretase endoprotease activity occurred in the 3 assays (see FIG. 7). The assay conducted with aminopeptidase M and its basic pH buffer and that of the control assay having just the basic pH buffer produced approximately the same amount of fluorescence. This result is consistent with that obtained in Example IV, which showed that chromaffin vesicles contain an endogenous β-secretase methionine and lysine aminopeptidase.

EXAMPLE X

β-secretase Endoprotease Activity Obtained During Isolation of Chromaffin Vesicles The β-secretase endoprotease activity of fractions obtained during the isolation procedure described in Example I was determined at the pH optimum of 5.5, with and without DTT using the assay described in Example VII. The ratio of those activities (with/without DTT) was calculated and the ratios obtained for the fraction shown in Table I.

TABLE I

| FRACTION | RATIO |
| --- | --- |
| Adrenal Medulla Homgenate | 4.7 |
| Pellet from 1,500 rpm Centrifugation (nuclear fraction) | 11.6 |
| Pellet from 1st 8,800 rpm Centrifugation (crude vesicle fraction) | 3.2 |
| Pellet from 2nd 8,800 rpm Centrifugation (washed vesicle fraction) | 6.3 |
| Pellet from 25,000 rpm Discontinuous Gradient Centrifugation (vesicle fraction) | 11.0 |

The results show that β-secretase endoprotease activity is enriched in the nuclear fraction and the vesicle fraction. But, as described in Example VI, only the chromaffin vesicles contain the APP protein, and thus only in that fraction does the protease having β-secretase endoprotease activity also have access to the APP protein substrate.

EXAMPLE XI

Protease Inhibitors of β-secretase Endoprotease Activity in Chromaffin Vesicle Lysate The effect of various protease inhibitors on β-secretase endoprotease activity in the lysate was determined at the pH optimum 5.5 in the assay described in Example IX containing aminopeptidase M. Protease inhibitors specific for various protease classes were used. The protease inhibitor was added to each assay at the start of the reaction at the appropriate concentration. The extent of inhibition was expressed as a percentage of the activity without the inhibitor (control). Triplicate assays varied by less than 10%. The results are shown in Table II.

TABLE II

| PROTEASE CLASS | INHIBITOR (Concentration) | % CONTROL |
| --- | --- | --- |
| Control | None | 100 |
| Cysteine | E64c (10 μM) | 0 |
| Cysteine | pHMB (1 mM) | 35 |
| Serine | PMSF (100 μM) | 58 |
| Serine | Chymostatin (10 μM) | 11 |
| Aspartyl | Pepstatin A (10 μM) | 78 |
| Metallo | EDTA (1 mM) | 100 |
| Metallo | EGTA (1 mM) | 99 |
| Nonspecific | Leupeptin (100 μM) | 0 |

The results show that the β-secretase endoprotease activity in the chromaffin vesicle lysate was completely inhibited by the cysteine protease class inhibitor E64c, and the nonspecific protease inhibitor leupeptin. The serine protease class inhibitor chymostatin and the cysteine protease inhibitor pHMB greatly inhibited activity. The apartyl protease class inhibitor pepstatin A slightly inhibited the activity and the metallo protease class inhibitors did not inhibit activity.

EXAMPLE XII

Isolation of β-Secretases from Chromaffin Vesicles

The chromaffin vesicle lysate was separated into 2 β-secretase endoprotease activity peaks (referred to as "Peak I" and "Peak II"). Peak I had about 3 times the total activity of Peak II and a different β-secretase endoprotease activity than did Peak II. The Peak I activity was very sensitive to the presence of aminopeptidase M in the assay whereas the Peak II activity was relatively insensitive to aminopeptidase M.

The Peak I center and range of activities had molecular weights of about 185 kDa, and about 180 to 200 kDa, respectively. Peak I was found to be a protease complex having a broad band of activity as determined by a native PAGE activity assay and 3 distinct activities corresponding to molecular weights of about 88, 81, and 61 kDa, in a non-reducing SDS-PAGE activity assay. Peak I was found to contain 3 proteins having molecular weights of about 88, 81, and 36 kDa, and 4 proteins having molecular weights of about 66, 60, 33, and 29 kDa, in a non-reducing and a reducing SDS-PAGE stained for proteins, respectively.

Peak II had a center and range of activities having molecular weights of about 65 kDa, and about 50 to 90 kDa, respectively. Peak II contained 2 proteins having different net electronegative charges and β-secretase endoprotease activity (referred to as "Peak II-A" and "Peak II-B").

Figure 8:
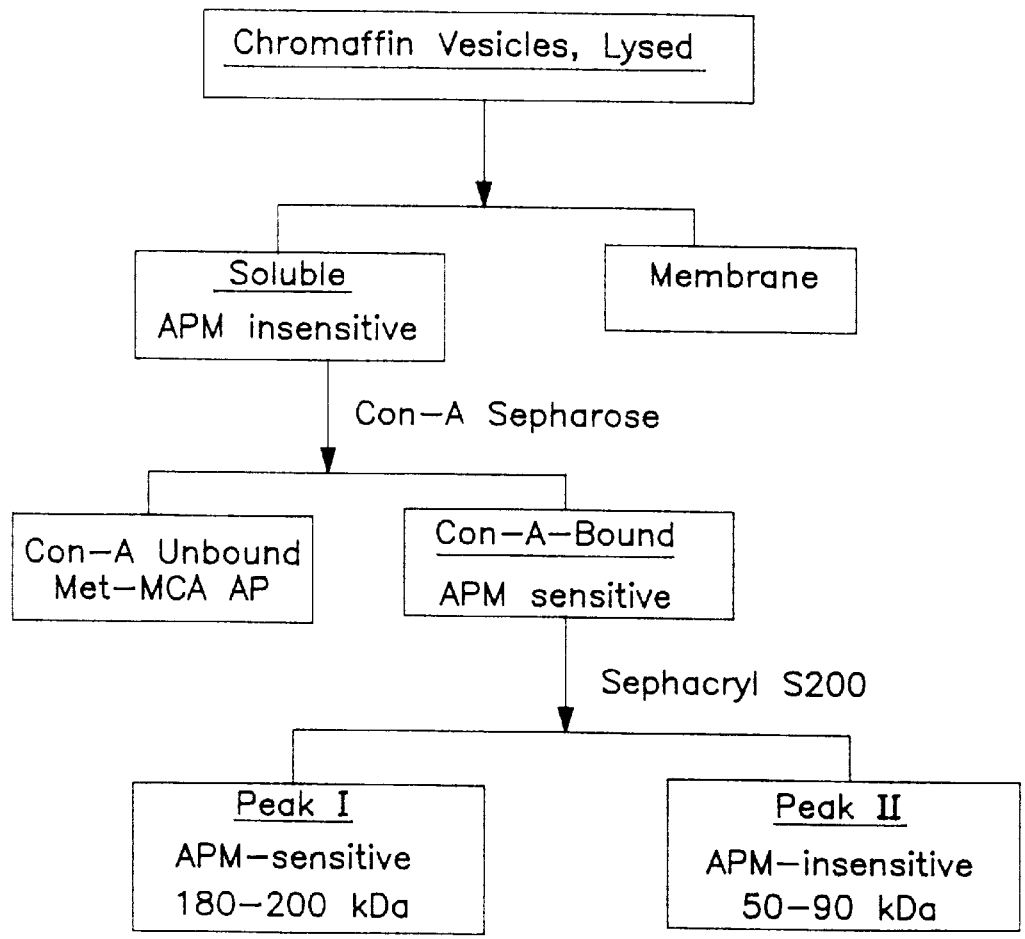
FIGS. 8. The isolation procedure used to obtain Peak I and Peak II is diagrammed.

Isolation of Peaks I and II and Characterization of the β-secretase Endoptotease Activites in those Peaks The procedure used to isolate Peaks I and II is diagramed in FIG. 8. The β-secretase endoprotease activity with and without aminopeptidase M was determined after each isolation step using the assay described in Example IX. Isolation steps that enriched that activity were selected. The total and specific activities after each isolation step are summarized in Example XIII. The β-secretase aminopeptidase activity was determined by the assay described in Example IV.

Preliminary experiments indicated that the β-secretase is present in chromaffin vesicles at a relatively low concentration. Thus, a very large number of bovine adrenal glands, approximately 2400, was used so that a sufficient amount the β-secretase could be obtained for analysis. Using the methods described in Example I, numerous chromaffin vesicle lysate preparations were made over a period of approximately 6 months and pooled.

A soluble extract and membrane pellet from the pooled lysate was made by ultracentrifugation at approximately 100,000×g. The bulk of the activity was in the soluble extract and was aminopeptidase insensitive (see Krieger, T. K. and Hook, V. Y. H. *J. Biol. Chem.* 266, 8376–8383, (1991). As such, it was concluded that the β-secretase endoprotease activity was not bound to the chromaffin vesicle membranes.

The soluble extract was separated by concanavalin A-Sepharose resin chromatography (referred to as "Con A") into bound and unbound fractions. The Con-A bound fraction was subsequently eluted using alpha-methylmannoside (referred to as the "eluted Con-A bound fraction") and contained the bulk of the β-secretase endoprotease activity, but no β-secretase aminopeptidase activity. The unbound fraction (referred to as the "Con-A unbound fraction"), in contrast, contained β-secretase methionine and lysine aminopeptidase activity, but little β-secretase endoprotease activity. The Con-A step thus separated the endogenous β-secretase endoprotease and aminopeptidase activities (see Krieger, T. K. and Hook, V. Y. H., ibid.).

Figure 9:
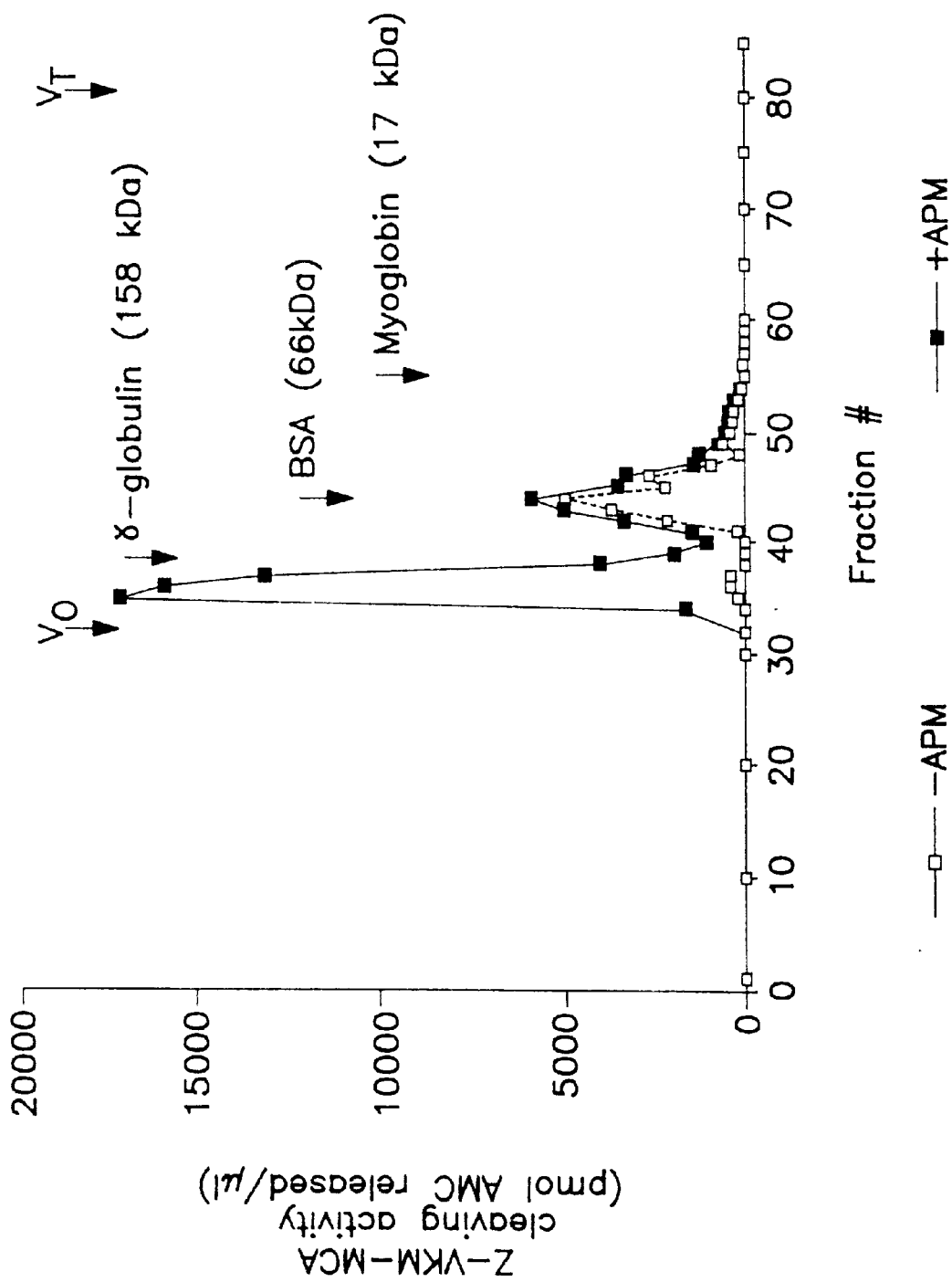
FIG. 9. The fluorescence activity is plotted as a function of the fraction number (#) obtained from the Sephacryl S200 in the procedure diagramed in FIG. 8. Fraction numbers 30 to 40, and 40 to 50 contain Peak I and Peak II, respectively. The activity is that which results from cleavage of the Z*Val-Lys-Met-MCA substrate by the fraction without aminopeptidase M (open squares), or with aminopeptidase M (closed squares). The fluorescence activity is in pmol of free MCA per microliter (AMC/µl). The γ-globulin, BSA, and myoglobin are calibration weight standards.

The contents of the eluted Con-A bound fraction were fractioned according to molecular size using a Sephacryl S200 column (Krieger, T. K. and Hook, V. Y. H. ibid.). That resulted in the Peak I and Peak II β-secretase endoprotease activities. The Peak I center and range of activities corresponded to proteins having molecular weights of approximately 185 kDa, and 180 to 200 kDa, respectively. The Peak II center and range of activities corresponded to proteins having molecular weights of approximately 65, and 50 to 90 kDa, respectively (see FIG. 9).

Peak I had more than 3 times the total activity of Peak II, but the Peak I activity without aminopeptidase M was only about 5% of that produced with the aminopeptidase. Thus, Peak I was aminopeptidase sensitive. Since Peak I alone did not produce much fluorescence, the majority of the Peak I activity does not cleave the Met-MCA bond in the Z*Val-Lys-Met-MCA substrate because cleavage of that bond must occur to produce fluorescent free MCA. But since the addition of aminopeptidase M produced a significant amount of fluorescence, the majority of the Peak I activity must endoproteolytically cleave that substrate because that cleavage must occur, for reasons discussed above, in order for the aminopeptidase M to cleave the Met-MCA bond and the Lys-Met bond and produce fluorescent free MCA. The Peak I activity thus must cleave the Lys-Met or the Val-Lys bond because those are the only other peptide bonds in the substrate that can be cleaved. Moreover, the fact that aminopeptidase M must be added to Peak I to detect activity confirms that the Con-A isolation step removed most of the endogenous aminopeptidases from the eluted Con-A bound fraction.

As discussed above, the Met-MCA bond in the Z*Val-Lys-Met-MCA substrate is a mimic of the β-secretase scissile bond Met-Asp in the APP protein. As such, failure of the Peak I β-secretase endoprotease to cleave the Met-MCA bond means that it also does not cleave the β-secretase scissile bond. Rather, as discussed below, the majority of the Peak I β-secretase endoprotease activity preferentially cleaves the Lys-Met in the β-secretase recognition site. Thus, for the Peak I β-secretase endoprotease to produce the amino terminal end of the Aβ peptide from an APP protein, several cleavages must occur. For example, the Peak I β-secretase endoprotease can cleave the Lys-Met bond adjacent to the β-secretase scissile bond and, second, an endogenous β-secretase aminopeptidase can cleave off the amino terminal Met in the β-secretase scissile bond Met-Asp to produce the amino terminal end of the Aβ peptide. Alternatively, the Peak I β-secretase endoprotease can cleave the Val-Lys bond and an endogenous β-secretase aminopeptidase(s) subsequently cleave off the Lys and Met amino acids and produce the amino terminal end of the Aβ peptide.

In contrast, Peak II was relatively aminopeptidase insensitive as its activity without aminopeptidase M was about 84% of that with the aminopeptidase. Thus, the majority of the Peak II activity cleaves the Met-MCA bond in the substrate Z*Val-Lys-Met-MCA directly because Peak II alone produces fluorescent free MCA. As the Met-MCA bond is a mimic of the β-secretase scissile bond, the majority of Peak II β-secretase endoprotease activity also cleaves the β-secretase scissile bond which can directly produce the amino terminal end of the Aβ peptide.

But the modest increase in the fluorescence produced by Peak II with aminopeptidase M indicates that some of the Peak II activity also cleaves the Lys-Met or the Val-Lys bond in the Z*Val-Lys-Met-MCA substrate for reasons described above regarding Peak I. Similarly, some of the Peak II activity also can produce the amino terminal end of the Aβ peptide by a combination of endoprotease and aminopeptidase cleavages as discussed above regarding Peak I.

These results demonstrate that multiple β-secretases are involved in producing an Aβ peptide from an APP protein.

Isolation of β-secretases from Peak I

Figure 10:
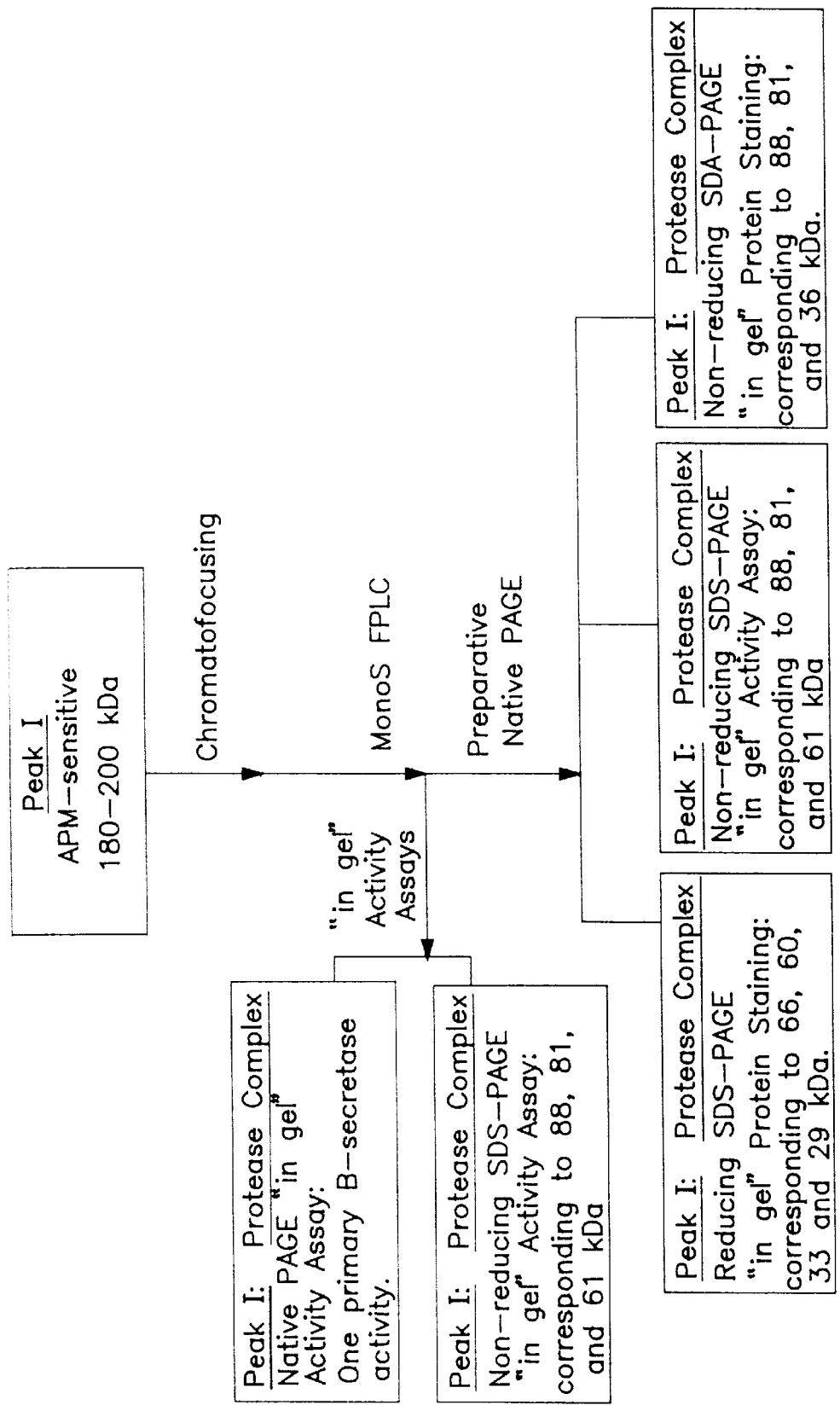
FIG. 10. The procedure used to isolate the β-secretases from Peak I is diagramed.

The procedure used to isolate the β-secretases from Peak I is diagramed in FIG. 10. The Sephacryl S200 column fractions containing the Peak I β-secretase endoprotease activity were pooled (referred to as the "Peak I Sephacryl S200 fraction") and chromatographed on a chromatofocusing Polybuffer Exchange 94 column (PHARMACIA, Piscataway, N.J., referred to here as "CF"). The CF fractions containing the β-secretase endoprotease activity were pooled and concentrated with buffer exchange to 100 mM citric acid-NaOH, pH 4.5, using an AMICON ultrafiltration apparatus equipped with a YM 10 membrane. (referred to as the "Peak I CF fraction" or "CF fraction," see Krieger, T. K. and Hook, V. Y. H., ibid.).

The Peak I CF fraction, in turn, was purified using cation Mono S exchange chromatography by FPLC (referred to as "Mono S"). The CF fraction was loaded onto a Mono S ion exchange FPLC column (1 ml HiTrap column SP, PHARMACIA, Piscataway, N.J.) that was equilibrated with 100 mM citric acid-NaOH, pH 4.5 (referred to as "buffer A"). The column was eluted with a NaCl gradient generated with a buffer consisting of 100 mM citric acid-NaOH, pH 4.5, 2.0 M NaCl (referred to as "buffer B"), with the gradient consisting of 0% buffer B at 1–15 min., 0–25% buffer B at 15–45 min., 25–100% buffer B at 45–50 min., 100% buffer B at 50–55 min., 100–0% buffer B at 55–60 min., and 0% buffer B at 60–75 min., with a flow rate of 1 ml/min. Fractions containing β-secretase endoprotease activity were pooled and concentrated by AMICON ultrafiltration with buffer exchange to 100 mM citric acid-NaOH, pH 4.5 (referred to as the "Peak I Mono S fraction" or "Mono S fraction").

The Mono S fraction was further analyzed by various polyacrylamide gel electrophoresis (PAGE) methods. Referring in FIG. 10, one such method was a "native PAGE in gel activity assay," which determined the β-secretase endoprotease activity of the Mono S fraction in the PAGE gel. In this assay, the proteins are first separated by electrophoresis and then allowed to proteolytically react with a suitable substrate in the gel. Proteins having proteolytic activity are identified by the formation of a cleavage product in the gel. A suitable substrate and cleavage product for detecting a secretase in this assay is an APP substrate and an APP derived product. The APP derived product can be detected by various methods such as those described above, but fluorescent detection methods are preferred. The PAGE in gel activity assay can also be used to detect proteases other than secretases using suitable substrates. The in gel activity assay may also use other suitable gels, such as, for example, agarose. In contrast to the PAGE in gel protein staining assays described below, the PAGE in gel activity assay determines only those proteins having protease activity rather than all proteins.

In a native PAGE in gel activity assay, the sample is in a solution which preserves protein complexes composed of proteins associated together by non-covalent and covalent bonds in their "native" state. Thus, a native PAGE in gel activity assay can determine the proteolytic activity of a protein complex. If a protein complex has such activity, that complex is referred to as a "protease complex." A protease complex is two or more proteins associated together by a non-covalent bond, such as, for example, an ionic bond, or a non-peptide covalent bond, such as, for example, a disulfide bond, and at least one of the proteins has protease activity. A β-secretase protease complex is a protease complex that cleaves an APP substrate.

Referring to FIG. 10, another PAGE method that the Mono S fraction was subjected is the "non-reducing SDS-PAGE in gel activity assay." Like the native PAGE in gel activity assay, the non-reducing SDS-PAGE in gel activity assay also determined the β-secretase endoprotease activity of the Mono S fraction in the PAGE gel. But this assay differs in that it contains the detergent SDS, hence the term "SDS-PAGE." SDS separates proteins associated together by a non-covalent bond. A "non-reducing in gel assay" means that the assay does not contain a reducing agent, such as, for example, β-mercaptoethanol. Such reducing agents sever covalent disulfide bonds between and within proteins. Thus, in the non-reducing SDS-PAGE in gel activity assay, proteins associated by a non-covalent bond are separated from each other but those proteins that are linked by a disulfide bond are not.

The substrate used in all in gel activity assays was the peptide Z*Phe-Arg-MCA (PENINSULA LABORATORIES, San Carlos, Calif.). The Phe-Arg-MCA sequence of that sequence mimics the Val-Lys-Met sequence in the β-secretase recognition site because both contain a hydrophobic amino acid adjacent to a positively charged amino acid and the MCA group, as discussed above, mimics a P1' amino acid. As such, cleavage of the Arg-MCA bond in the Z*Phe-Arg-MCA substrate is equivalent to cleaving the Lys-Met bond in the β-secretase recognition site or in the Z*Val-Lys-Met-MCA substrate. That later substrate was not used for the in gel assay because, as discussed above, an aminopeptidase is required to detect cleavage of that substrate by Peak I.

Native PAGE in gel activity assays were conducted as follows. The Z*Phe-Arg-MCA substrate was embedded into the gel by copolymerization of Z*Phe-Arg-MCA (250 μM) with resolving gel (8 7×0.1 cm, NOVEX gel cassette, San Diego, Calif.) components consisting of 12% polyacrylamide with 0.16% bis-acrylamide and 0.375 Tris-HCl, pH 8.8. The stacking gel was 6% polyacrylamide, 0.16% bis-acrylamide, and 0.125 M Tris-HCl, pH 6.8, prepared according to Laemmli (Laemmli, U. K. *Nature* 227:259, 680–685 (1970)). The Mono S fraction (2–4 μl) was prepared in native sample buffer containing 50 mM Tris-HCl, pH 8.3, and 2% glycerol, and electrophoresed in the gel at 4° C. in a running buffer consisting of 25 mM Tris-HCl, 192 mM glycine, pH 8.3 for 2.5 hours at a constant current of 25 mAmp. The gel was then washed in cold 2.5% Triton X-100 solution for 10 minutes, and with cold sterile water for 10 minutes. β-secretase endoprotease cleavage of the substrate Z*Phe-Arg-MCA embedded in the gel was conducted by incubating the gel at 37° C. for 2 hours in 100 mM citric acid-NaOH, pH 5.0, 1 mM EDTA, 1 mM DTT, and 10 mM CHAPS. AMC fluorescence in the gel was visualized under a UV transilluminator. The fluorescent image was photographed with Kodak DC120 digital camera, and analyzed with the EDAS120 image software system, which allows quantitative image analysis.

The native PAGE in gel activity assay of the Peak I Mono S fraction resulted in a wide broad band of faint fluorescence. That result is characteristic of a protease complex and shows that the activity in Peak I is due to a protease complex. Moreover, the result shows that the protease complex cleaves the Arg-MCA bond because that cleavage must occur for fluorescence to be detected and fluorescence was detected without an aminopeptidase being present. Since the Arg-MCA bond in the Z*Phe-Arg-MCA substrate is equivalent to the Lys-Met bond in the β-secretase recognition site, the protease complex also cleaves the Lys-Met bond in that substrate.

The non-reducing SDS-PAGE in gel activity assay was conducted as described for the native PAGE in gel activity assay, except that the stacking and resolving gels contained 0.1% SDS, the sample buffer contained 1.5% SDS, and the electrophoresis was conducted for 1.5 hours. The non-reducing SDS-PAGE in gel activity assay showed 3 distinct, precise and intense fluorescent bands corresponding to proteins having molecular weights of approximately 88, 81, and 66 kDa. The 3 proteins cleaved the Arg-MCA bond in the Z*Phe-Arg-MCA substrate because fluorescence was produced without aminopeptidase. Moreover, those proteins also cleave the Lys-Met bond in the β-secretase recognition site for the reasons discussed above.

The Peak I Mono S fraction was also subjected to "preparative native PAGE." This electrophoresis method was used to further isolate the β-secretases. Native conditions using the MiniPrep Cell system (BIORAD, Richmond, Calif.). Tube gels (7 mm internal diameter) were prepared with the resolving gel (10 cm) consisting of 6% polyacrylamide (with 0.16% bis-acrylamide and 0.375 M Tris-HCl, pH 8.8) and a stacking gel (1 cm) of 4% polacrylamide (with 0.11% bis-acrylamide and 0.125 M Tris-HCl, pH 6.8), prepared according to the manufacturer's protocol. The Mono S fraction (200 to 300 μl) in native sample buffer containing 25 mM Tris-HCl, 192 mM glycine, pH 8.3, and 10% glycerol was subjected to electrophoresis in the native tube gel at a constant power of 1 watt at 4° C. for 48 hours in running buffer consisting of 25 mM Tris-HCl, 192 mM glycine, and pH 8.3. During electrophoresis, fractions (0.6 ml/fraction) were eluted in running buffer at a flow rate of 0.02 ml/minute; stability of eluted β-secretase endoprotease activity was improved with adjustment of fractions to pH 6.0 using an equal volume of 0.1 M citric acid-NaOH, pH 4.5. Fractions were immediately assayed for Z*Val-Lys-Met-MCA cleavage in the presence of aminopeptidase M, or for Z-Phe-Arg-MCA without aminopeptidase M as described (Azaryan, A. V. and Hook, V. Y. H., FEBS Lett. 341, 197–202 (1994)). After preparative native gel electrophoresis, one peak of β-secretase endoprotease activity was observed for cleavage of the substrate Z*Val-Lys-Met-MCA.

The preparative native PAGE sample containing the activity was further analyzed by various PAGE methods, including the non-reducing SDS-PAGE in gel activity assay described above. That assay resulted in the same 3 activity bands having molecular weights of about 88, 81, and 61 kDa obtained from the Mono S fraction run in that assay.

The preparative native PAGE sample was also analyzed in a non-reducing SDS-PAGE in gel protein staining assay which detects the proteins present in the gel. In contrast to the in gel activity assay, the protein staining assay detects all proteins present in a sufficient amount to be detected without regard to protease activity. The non-reducing SDS-PAGE in gel protein staining assay was conducted in a similar manner as the activity assay, but was silver stained to identify the proteins and resulted in 3 definite and precise bands corresponding to proteins having molecular weights of about 88, 81, and 36 kDa.

The results obtained from the non-reducing SDS-PAGE in gel protein staining and activity assays were compared. The 88 and 81 kDa proteins observed by silver staining correlated with the two β-secretase endoproteolytic activities at those weights in the activity assay. But no protein was detected in the protein staining assay corresponding to the 61 kDa activity band. This result implied that the amount of protein at that position may have been insufficient to be detect by silver staining. If that is the case, the 61 kDa protein had a very high specific activity because intense activity was observed at that position. No activity was detected in the activity assay at the position corresponding to the 36 kDa protein, indicating that the 36 kDa protein does not have β-secretase endoproteolytic activity.

The preparative native PAGE sample was further analyzed in a reducing SDS-PAGE in gel protein staining assay. Like the staining assay described above, this assay also detected the proteins present in the gel without regard to proteolytic activity. But since this assay was conducted in the presence of a reducing agent, β-mercaptoethanol, disulfide bonds were severed. The assay was run as described above for the protein staining assay except that the gel and sample buffer contained β-mercaptoethanol. Four proteins having molecular weights of approximately 66, 60, 33, and 29 kDa were detected.

The reducing SDS-PAGE in gel protein staining assay resulted in more and on average proteins of lower molecular weight than did the corresponding non-reducing assay. That difference indicates that the preparative native PAGE sample contained proteins having disulfide bonds which were severed by the reducing agent to produce a larger number of proteins with lower molecular weights. In particular, the 88 and 81 kDa proteins had such bonds severed because only lighter proteins were observed under reducing conditions. The 33 and 36 kDa proteins obtained under reducing and non-reducing conditions may be the same protein because their weights are similar.

The results obtained from the reducing SDS-PAGE in gel protein staining and the non-reducing SDS-PAGE in gel activity assays were compared. The 88 and 81 kDa proteins having activities contained one or more disulfide bonds that were severed under the reducing conditions. The 60 kDa and 61 kDa proteins in silver staining and activity assays were about the same weight and may be the same protein.

Isolation of β-secretases from Peak II

Figure 11:
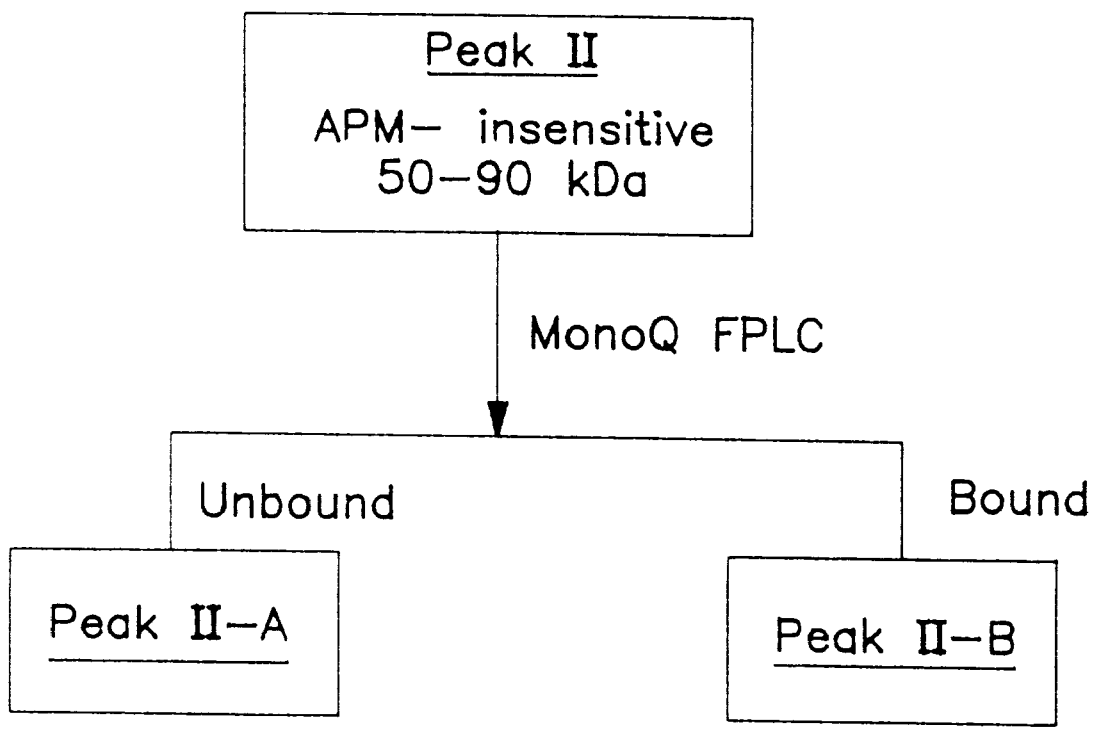
FIG. 11. The procedure sued to isolate the β-secretases from Peak II is diagramed.

The procedure used to isolate Peak II-A and Peak II-B from Peak II is diagramed in FIG. 11. The Sephacryl S200 fractions containing Peak II were pooled and further purified using Mono Q ion exchange FPLC chromatography (referred to as "Mono Q FPLC"). The fraction that did not bind to that column contained Peak II β-secretase endoprotease activity (referred to as the "unbound Peak II" or "Peak II-A"). The fraction that bound to the column was eluted using a NaCl gradient from zero to 0.5 M NaCl, and also contained Peak II β-secretase endoprotease activity (referred to as "bound Peak II" or the "Peak II-B"). Peak II-B was further purified by a second Mono Q column, with elution of the β-secretase activity by a pH gradient of pH 7.0 to pH 4.0 generated by polybuffer 74 (PHARMACIA, Piscataway, N.J.), performed as described previously (Krieger, T. K. and Hook, V. Y. H., ibid.). Since Mono Q FPLC is an anion exchange chromatography, the unbound Peak II is a protein that is less electronegative than the Peak II-B protein.

EXAMPLE XIII

β-secretase Endoprotease Activities Obtained
During Isolation of β-secretases

The total (relative fluorescence units/0.5 hr) and specific (relative fluorescence units/mg protein) of the β-secretase endoprotease activity without and with aminopeptidase M (−APM, +APM, respectively) was determined for fractions obtained in the isolation procedure described in Example XII. All assays were conducted as described in Example IX. The activities obtained are summarized in Table III.

TABLE III

| ISOLATION STEP | TOTAL ACTIVITY –APM | TOTAL ACTIVITY +APM | SPECIFIC ACTIVITY –APM | SPECIFIC ACTIVITY +APM |
|---|---|---|---|---|
| Lysate | 11 | 12 | 1.8 | 1.9 |
| Soluble extract | 12 | 12 | 2.6 | 2.5 |
| Membrane | 0.4 | 0.6 | 1.7 | 2.3 |
| Con-A bound[a] | 19 | 75 | 367 | $1.5 \times 10^3$ |
| Con-A unbound[b] | 8 | 9 | 2 | 2 |
| *Peak I* | | | | |
| Sephacryl S200 | 13 | 275 | $2.0 \times 10^3$ | $4.2 \times 10^4$ |
| CF fraction | 38 | 496 | $3.0 \times 10^3$ | $3.8 \times 10^4$ |
| Mono S fraction | 16 | 300 | $5.0 \times 10^5$ | $9.3 \times 10^6$ |
| Prep. SDS-PAGE | ND[c] | 30 | $1.0 \times 10^7$ | $2.0 \times 10^7$ |
| *Peak II* | | | | |
| Sephacryl S200 | 63 | 75 | $6.0 \times 10^4$ | $7.2 \times 10^4$ |
| Mono Q FPLC Peak II-A | 15 | 16 | $5.5 \times 10^5$ | $6.0 \times 10^5$ |
| Mono Q FPLC Peak II-B | 6 | 6 | $3.1 \times 10^4$ | $4.4 \times 10^4$ |

[a]No β-secretase aminopeptidase activity detected
[b]β-secretase aminopeptidase activity detected
[c]Not done The total activity of the lysate and the soluble extract without aminopeptidase M was about 92% and 100% of that with the aminopeptidase, respectively, and thus were aminopeptidase insensitive. The soluble extract contained about 100% of the total activity in the lysate, but the membrane pellet contained only about 4% of that activity, indicating that the β-secretase endoprotease activity is not bound to the chromaffin vesicle membranes.

The eluted Con-A bound fraction assayed without and with aminopeptidase M had about 158% and 625% of the total activity in the lysate, respectively. The increase in the total activity indicated that an inhibitor or competitive substrate, such as APP protein, may be removed at this step. The eluted Con-A bound fraction had a total activity that was somewhat aminopeptidase sensitive as the activity without aminopeptidase M was approximately 25% of that with the aminopeptidase.

The Con-A unbound fraction contained the endogenous β-secretase aminopeptidase activity which was not present in the eluted Con-A bound fraction. As such, Peak I and Peak II subsequently purified from the eluted Con-A bound fraction did not contain significant endogenous aminopeptidase activity.

Peak I from the Sephacryl S200 isolation step was highly aminopeptidase sensitive, having a total activity of only about 4.7% without aminopeptidase M as and with the aminopeptidase. Moreover, Peak I assayed with the aminopeptidase had about 367% and 2292% of the total activity in the eluted Con-A bound fraction and lysate, respectively, again indicating possible removal of an inhibitor or competitive substrate.

Continuing with the isolation of Peak I, the CF fraction also was aminopeptidase sensitive as the total activity without aminopeptidase M was about 7.6% of that with the aminopeptidase. Again the total activity was increased, this time by about 180% and 4,133% of that from the Sephacryl S200 fraction and the lysate, respectively, as measured with aminopeptidase M and again raising the possibility that an inhibitor or competitive substrate was removed.

The Mono S fraction of Peak I remained very aminopeptidase sensitive, having a total activity without aminopeptidase M of about 5.3% of that with the aminopeptidase. But the total activity of the Mono S fraction was about 60% and 2,500% of that in the CF fraction and lysate, respectively. This indicates that the Mono S isolation step may lose some activity but that the activity remains well above that in the lysate.

The preparative SDS-PAGE isolation of Peak I resulted in 10% and 250% of the activity in the Mono S fraction and lysate, respectively. Moreover, the activity after this step, unlike the previous isolation steps, became quite unstable indicating that the preparative SDS-PAGE isolation step may remove an activator or stabilizing agent.

Returning to the isolation of Peak II by Sephacryl S200, the Peak II had about 27% of the activity of Peak I. In other words, Peak I had about 3 times more β-secretase endoprotease activity than did Peak II. But Peak II was relatively aminopeptidase insensitive as the total activity without aminopeptidase M was about 84% of that with the aminopeptidase. Peak II total activity assayed with aminopeptidase M was the same as that in the eluted Con-A bound fraction indicating that this isolation step does not remove an inhibitor, an APP substrate, an activator, or a stabilizing agent.

After Mono Q FPLC isolation, Peak II-A and Peak II-B were found to be aminopeptidase insensitive. The combined total activity of Peak II-A and Peak II-B was about 32% of the total activity in the Sephacryl S200 fraction with aminopeptidase M. Peak II-A and Peak II-B had a total activity of about 133% and 66% of that in the lysate, respectively.

The specific activity showed that a very high degree of isolation was obtained. Specifically, the preparative SDS-PAGE electrophoresis isolation step of Peak I resulted in about a $0.5 \times 10^6$ and $1.0 \times 10^6$ purification from the chromaffin vesicle lysate as analyzed without and with aminopeptidase, respectively. The Mono Q FPLC isolation of Peak II-A resulted in a $2.3 \times 10^5$ and $3 \times 10^5$ purification from the chromaffin vesicle lysate as analyzed without and with aminopeptidase, respectively. The Mono Q FPLC isolation step of the Peak II-B resulted in a $1.5 \times 10^4$ and $2.2 \times 10^4$ purification from the chromaffin vesicle lysate as analyzed without and with aminopeptidase, respectively.

EXAMPLE XIV

Protease Inhibitors of β-secretase Endoprotease Activity in Peaks I and II

The effect of various protease inhibitors on β-secretase endoprotease activity in Peaks I and II was determined by the method described in Example XI. The results were expressed as a percent inhibition of the control (no inhibitor) is summarized in Table IV.

TABLE IV

| PROTEASE CLASS | INHIBITOR (Concentration) | Peak I (%) | Peak II (%) |
|---|---|---|---|
| Control | None | 100 | 100 |
| Cysteine | E64c (10 μM) | 0 | 0 |
| Cysteine | pHMB (1 mM) | 67 | 68 |
| Serine | PMSF (100 μM) | 90 | 112 |
| Serine | Chymostatin (10 μM) | 0 | 35 |
| Aspartyl | Pepstatin A (100 μM) | 85 | 132 |
| Metallo | EDTA (1 mM) | 99 | 138 |
| Metallo | EGTA (1 mM) | 108 | 142 |
| Metallo | 1,10 Phenanthroline (500 μM) | 31 | 72 |
| Nonspecific | Leupeptin (100 μM) | 0 | 0 |

Peak I and Peak II activities were maximally inhibited by the nonspecific protease class inhibitor leupeptin, the cysteine class inhibitor E64c, and the serine protease class inhibitor chymostatin. The other cysteine class inhibitor, pHMB, slightly inhibited both activities. The other serine protease class inhibitor, PMSF, did not significantly inhibit either activity. The metallo protease class inhibitor 1,10 phenanthroline significantly inhibited Peak I, but only slightly inhibited Peak II. The other metallo protease class inhibitors and the aspartyl protease class inhibitor pepstatin A did not significantly inhibit either activity.

Peak I and Peak II activities were identically inhibited by the cysteine protease class and nonspecific protease class inhibitors. The serine, aspartyl and metallo protease classes inhibitors tended to inhibit Peak I activity more than Peak II.

The inhibition of Peak I and Peak II activities was compared with that obtained for the chromaffin vesicle lysate (Example XI). All 3 activities were completely inhibited by the cysteine protease class inhibitor E64c and the nonspecific protease class inhibitor leupeptin. The serine protease class inhibitor chymostatin and the cysteine protease class inhibitor pHMB inhibited all activities, although the Peak I and Peak II activity was inhibited less than that of the lysate. The serine protease class inhibitor PMSF significantly inhibited the lysate activity but only slightly inhibited the Peak I and Peak II activities. The aspartic protease class inhibitor pepstatin A slightly inhibited the lysate and Peak I activities but increased the activity of Peak II. Except for the 1,10 phenanthroline, none of the metallo class protease class inhibitors inhibited any activity and, in some cases, increased the activity.

EXAMPLE XV

Confirmation of Cleavage Specificities of the Peak I, Peak II-A, and Peak II-B β-Secretase Endoprotease Activities As discussed above, the substrates Z*Val-Lys-Met-MCA and Z*Phe-Arg-MCA mimic the β-secretase recognition site in the APP protein. The fluorescent MCA that resulted from the cleavage of those substrates established the cleavage specificities of the Peak I, Peak II-A, and Peak II-B β-secretases. In particular, those results showed that the majority of the endoprotease activity in Peak I cleaved the Lys-Met bond amino terminally adjacent to the β-secretase scissile bond in the β-secretase recognition site of the APP protein. Those results also showed that the majority of the endoprotease activity in Peak II-A and Peak II-B cleaved the β-secretase scissile bond in the β-secretase recognition site of the APP protein.

To confirm the Peak I cleavage specificity, electrospray mass spectrometry (EMS) was also used to analyze the APP derived products resulting from the cleavage of the Z*Val-Lys-Met-MCA substrate by the Peak I activity. The cleavage assay was conduced by the method described in Example XII without aminopeptidase M. The APP derived products were then analyzed by a commerical EMS facility (SCRIPPS RESEARCH INSTITUTE, La Jolla, Calif.). The EMS analysis confirmed that the Peak I activity cleaved the Lys-Met bond in the Z*Val-Lys-Met-MCA substrate.

To confirm the cleavage specificities of the Peak I, Peak II-A, Peak II-B activities, another APP substrate was reacted with each of those activities and the APP derived products analyzed by EMS. The APP substrate Ser-Glu-Val-Lys-Met-Asp-Ala-Glu-Phe (SEQ ID NO.:5) contains the 5 amino terminal and 4 carboxyl terminal amino acids to the β-secretase scissile bond in the APP protein. The substrate was commercially produced and purified to greater 95% purity by standard reverse phase high pressure liquid chromatography methods. The cleavage assay of Example XII was used without the aminopeptidase M and without the Z*Val-Lys-Met-MCA substrate, but with the Ser-Glu-Val-Lys-Met-Asp-Ala-Glu-Phe (SEQ ID NO.:5) substrate (14 μg/assay). The APP derived products were then subjected to a C8 reverse phase high pressure liquid chromatography, eluted with an acetonitrile gradient in 0.1% TFA (trifluoroacetic acid), the peptides identified by absorbance spectroscopy at 210–215 nm and collected (see Krieger T. K. and Hook V. Y. H., ibid. and Krieger et al., *J. Neurochem.* 59, 26–31 (1992)). The EMS data of the eluted APP derived products confirmed that the majority of Peak I activity cleaved the Lys-Met bond and that the majority of the Peaks II-A and II-B activities cleaved the Met-Asp bond.

The above-identified references are expressly incorporated herein. Although the invention has been described with reference to the examples provided above, it should be understood that various modifications can be made without departing from the spirit of the invention. Accordingly, the invention is limited only by the claims.

I claim:

1. An isolated β-secretase comprising a protein having a molecular weight selected from the group consisting of about 61, 81 and 88 kiloDaltons (kDa) as determined by cleavage of an amyloid precursor protein (APP) substrate in a non-reducing sodium dodecyl sulfate polyacrylamide gel electrophoreis (SDS-PAGE) in gel activity assay.

2. The β-secretase of claim 1, wherein the protein cleaves the APP substrate at a β-secretase recognition site.

3. The β-secretase of claim 2, wherein the protein cleaves the β-secretase recognition site at a bond selected from the group consisting of Lys-Met and Val-Lys.

4. The β-secretase of claim 3, wherein the protein cleaves the Lys-Met bond.

5. The β-secretase of claim 3, wherein the protein cleaves the Val-Lys bond.

6. The β-secretase of claim 1, wherein the protein has a molecular weight of 61 kDa.

7. The β-secretase of claim 1, wherein the protein has a molecular weight of 81 kDa.

8. The β-secretase of claim 1, wherein the protein has a molecular weight of 88 kDa.

9. The β-secretase of claim 1, wherein the protein is obtained from substantially pure vesicles.

10. The β-secretase of claim 9, wherein the substantially pure vesicles are chromaffin vesicles.

11. The β-secretase of claim 10, wherein the chromaffin vesicles are bovine chromaffin vesicles.

* * * * *

SEQUENCE LISTING

<160> NUMBER OF SEQ ID NOS: 6

<210> SEQ ID NO 1
<211> LENGTH: 53
<212> TYPE: PRT
<213> ORGANISM: mammalian

<400> SEQUENCE: 1

```
Val Lys Met Asp Ala Gly Phe Arg His Asp Ser Gly Tyr Glu Val His
  1               5                  10                  15

His Gln Lys Leu Val Phe Phe Ala Glu Asp Val Gly Ser Asn Lys Gly
                 20                  25                  30

Ala Ile Ile Gly Leu Met Val Gly Gly Val Val Ile Ala Thr Val Ile
             35                  40                  45

Val Ile Thr Leu Val
         50
```

```
<210> SEQ ID NO 2
<211> LENGTH: 4
<212> TYPE: PRT
<213> ORGANISM: mammalian

<400> SEQUENCE: 2

Val Lys Met Asp
  1

<210> SEQ ID NO 3
<211> LENGTH: 4
<212> TYPE: PRT
<213> ORGANISM: mammalian

<400> SEQUENCE: 3

Gly Val Val Ile
  1

<210> SEQ ID NO 4
<211> LENGTH: 4
<212> TYPE: PRT
<213> ORGANISM: mammalian

<400> SEQUENCE: 4

Val Ile Ala Thr
  1

<210> SEQ ID NO 5
<211> LENGTH: 4
<212> TYPE: PRT
<213> ORGANISM: mammalian

<400> SEQUENCE: 5

Ile Ala Thr Val
  1

<210> SEQ ID NO 6
<211> LENGTH: 9
<212> TYPE: PRT
<213> ORGANISM: mammalian

<400> SEQUENCE: 6

Ser Glu Val Lys Met Asp Ala Glu Phe
  1               5
```